(12) United States Patent
Joddar et al.

(10) Patent No.: US 12,187,888 B2
(45) Date of Patent: Jan. 7, 2025

(54) DEVELOPMENT AND CHARACTERIZATION OF F-GELATIN ELECTROSPUN SCAFFOLDS FOR CARDIAC TISSUE MODELING

(71) Applicant: Board of Regents, The University of Texas System, Austin, TX (US)

(72) Inventors: Binata Joddar, El Paso, TX (US); David A. Roberson, El Paso, TX (US); Naveen Nagiah, El Paso, TX (US); Zayra N. Dorado, El Paso, TX (US); Ivana Hernandez, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 121 days.

(21) Appl. No.: 18/302,553

(22) Filed: Apr. 18, 2023

(65) Prior Publication Data
US 2023/0374299 A1 Nov. 23, 2023

Related U.S. Application Data

(60) Provisional application No. 63/364,834, filed on May 17, 2022.

(51) Int. Cl.
*A61L 15/32* (2006.01)
*B29C 71/04* (2006.01)
(Continued)

(52) U.S. Cl.
CPC .............. *C08L 67/04* (2013.01); *C08L 89/00* (2013.01); *C12N 5/0062* (2013.01);
(Continued)

(58) Field of Classification Search
CPC ....... A61L 15/32; B29C 71/04; C07D 307/52; C08J 3/24; C08J 3/28; C08L 67/04; C08L 89/06; C08L 101/14; D01D 5/003; D01D 5/0038; D01D 5/0046; D01D 5/34; D01F 8/14; D06M 10/001
(Continued)

(56) References Cited

U.S. PATENT DOCUMENTS

| | | | |
|---|---|---|---|
| 6,458,386 B1 * | 10/2002 | Schacht | C08L 89/06 424/443 |
| 8,048,446 B2 | 11/2011 | Lelkes et al. | |
| 2004/0063780 A1 * | 4/2004 | Matsuoka | C07D 307/52 514/471 |

OTHER PUBLICATIONS

Huang et al., "Electrospinning and mechanical characterization of gelatin nanofibers," Polymer, vol. 45, Issue 15, Jul. 12, 2004, 8 pages.https://www.sciencedirect.com/science/article/abs/pii/S0032386104003684.
(Continued)

*Primary Examiner* — Leo B Tentoni
(74) *Attorney, Agent, or Firm* — Yee & Associates, P.C.

(57) ABSTRACT

Cardiac tissue-on-a-chip platforms aimed at mimicking human cardiac tissue structures, are valuable tools to model, and serve as preclinical platforms for drug testing or therapies for cardiac repair. We have developed three types of electrospun scaffolds including furfuryl gelatin (f-gelatin) alone, with polycaprolactone (PCL) in the ratio of f-gelatin and PCL (1:1), and coaxial scaffolds with PCL (core) and f-gelatin (sheath). Scaffolds were developed through single nozzle electrospinning and coaxial electrospinning, respectively, to serve as scaffolds for cardiac tissue-on-a-chip platforms.

20 Claims, 18 Drawing Sheets

(51) Int. Cl.

| | |
|---|---|
| C07D 307/52 | (2006.01) |
| C08J 3/24 | (2006.01) |
| C08J 3/28 | (2006.01) |
| C08L 67/04 | (2006.01) |
| C08L 89/00 | (2006.01) |
| C08L 89/06 | (2006.01) |
| C08L 101/14 | (2006.01) |
| C12N 5/00 | (2006.01) |
| C12N 5/077 | (2010.01) |
| D01D 5/00 | (2006.01) |
| D01D 5/34 | (2006.01) |
| D01F 8/14 | (2006.01) |
| D06M 10/00 | (2006.01) |

(52) U.S. Cl.
CPC ......... *C12N 5/0657* (2013.01); *D01D 5/0038* (2013.01); *D06M 10/001* (2013.01); *C08L 2203/12* (2013.01); *C12N 2500/38* (2013.01); *C12N 2513/00* (2013.01); *C12N 2533/30* (2013.01); *C12N 2533/54* (2013.01); *C12N 2537/10* (2013.01)

(58) Field of Classification Search
USPC .............. 264/172.15, 330, 331.11, 465, 494; 522/109, 153; 525/415; 549/492
See application file for complete search history.

(56) References Cited

OTHER PUBLICATIONS

Zhang et al., "Electrospinning of Gelatin Fibers and Gelatin/PCL Composite Fibrous Scaffolds," Journal of Biomedical Materials Research, Part B, Applied Biomaterials, vol. 72B, Issue 1, Jan. 15, 2005, 10 pages.https://pubmed.ncbi.nlm.nih.gov/15389493/.
Acun et al., "A Tissue Engineered Model of Aging: Interdependence and Cooperative Effects in Failing Tissues", Scientific Reports, Jul. 2017: 5051, pp. 1-10, DOI: 10.1038/s41598-017-05098-2.
Ahuja et al., "Cardiac Myocyte Cell Cycle Control in Development, Disease and Regeneration", Physiol Rev., Apr. 2007, 97(2): 521-544, doi: 10.1152/physrev.00032.2006.
Angele et al., "Engineering of Osteochondral Tissue with Bone Marrow Mesenchymal Progenitor Cells in a Derivatized Hyaluronan-Gelatin Composite Sponge", Tissue Engineering, 1999, vol. 5:6 pp. 545-553.
Anilkumar et al., "The applicability of furfuryl-gelatin as a novel bioink for tissue engineering applications", Journal of Biomedical Materials Research Part B: Applied Biomaterials, 2019, vol. 1078:2, pp. 314-323.
Asaria et al., "Acute myocardial infarction hospital admissions and deaths in England: a national follow-back and follow-forward record-linkage study", Lancet Public Health, Apr. 2017, pp. 191-201, vol. 2.
Baker et al, "Determining the mechanical properties of electrospun poly-ϵ-caprolactone (PCL) nanofibers using AFM and a novel fiber anchoring technique", Materials Science and Engineering C, 2016, vol. 59, pp. 203-212.
Begum et al, "A Method for Evaluating the Use of Fluorescent Dyes to Track Proliferation in Cell Lines by Dye Dilution", Cytometry Part A, 2013, vol. 83A, pp. 1085-1095.
Boskey et al., "Osteopontin-hydroxyapatite interactions in vitro: inhibition of hydroxyapatite formation and growth in a gelatin-gel", Bone and Mineral, 1993, vol. 22, pp. 147-159.
Boudou et al., "A Microfabricated Platform to Measure and Manipulate the Mechanics of Engineered Cardiac Microtissues", Tissue Engineering: Part A, 2012, vol. 18:9-10, pp. 910-919, DOI: 10.1089/ten.tea.2011.0341.
Bulcke et al., "Structural and Rheological Properties of Methacrylamide Modified Gelatin Hydrogels", Biomacromolecules, 2000, vol. 1, pp. 31-38.
Chan et al., "Scaffolding in tissue engineering: general approaches and tissue-specific considerations", Eur Spine J, 2008, 17 (Suppl 4):S467-S479, DOI 10.1007/s00586-008-0745-3.
Filby et al., "An Imaging Flow Cytometric Method for Measuring Cell Division History and Molecular Symmetry During Mitosis", 2011, Cytometry Part A, 2011, vol. 79A, pp. 496-506.
Fu et al., "Electrospun gelatin/PCL and collagen/PLCL scaffolds for vascular tissue engineering", International Journal of Nanomedicine, 2014, vol. 4:9, pp. 2335-2344.
Gizaw et al., "The Role of Electrospun Fiber Scaffolds in Stem Cell Therapy for Skin Tissue Regeneration", Med One. 2019 ; 4, doi:10.20900/mo.20190002.
Hashim et al., "Potential use of Fourier transform infrared spectroscopy for differentiation of bovine and porcine gelatins", Food Chemistry, 2010, vol. 118, pp. 856-860.
Ifkovits et al., "Review: Photopolymerizable and Degradable Biomaterials for Tissue Engineering Applications", Tissue Engineering, 2007, vol. 13:10, pp. 2369-2385.
Jalali et al, "Regulation of Endothelial Cell Adherence and Elastic Modulus by Substrate Stiffness", Cell Communication & Adhesion, 2015, vol. 22:2-6, pp. 79-89, http://dx.doi.org/10.1080/15419061.2016.1265949.
Johnson et al, "Coaxially-structured fibres with tailored material properties for vascular graft implant", Materials Science & Engineering C, 2019, vol. 97, pp. 1-11.
Kumar et al., "A Visible Light-Cross-Linkable, Fibrin—Gelatin-Based Bioprinted Construct with Human Cardiomyocytes and Fibroblasts", ACS Biomater Sci Eng, 2019, vol. 5(9), pp. 4551-4563, doi:10.1021/acsbiomaterials.9b00505.
Kuo et al., "Surface Modification of Gelatin Nanoparticles with Polyethylenimine as Gene Vector", Journal of Nanomaterials, vol. 2011, Article ID 646538, 5 pages, doi: 10.1155/2011/646538.
Lai, "Biocompatibility of chemically cross-linked gelatin hydrogels for ophthalmic use", J Mater Sci: Mater Med, 2010, vol. 21, pp. 1899-1911, doi 10.1007/s10856-010-4035-3.
Majid et al., "Natural Biomaterials for Cardiac Tissue Engineering: A Highly Biocompatible Solution", Frontiers in Cardiovascular Medicine, 2020, vol. 7, Article 554597.
Musunuru et al., "Induced Pluripotent Stem Cells for Cardiovascular Disease Modeling and Precision Medicine", Circ Genom Precis Med., Nov. 2018:e000043, pp. 1-30, doi: 10.1161/HCG.0000000000000043.
Muyonga et al., "Fourier transform infrared (FTIR) spectroscopic study of acid soluble collagen and gelatin from skins and bones of young and adult Nile perch (*Lates niloticus*)", Food Chemistry 86, 2004, pp. 325-332.
Nagiah et al., "Development and characterization of coaxially electrospun gelatin coated poly (3-hydroxybutyric acid) thin films as potential scaffolds for skin regeneration", Materials Science and Engineering C 33 (2013) 4444-4452.
Nagiah et al., "Electrospinning of poly (3-hydroxybutyric acid) and gelatin blended thin films: fabrication, characterization, and application in skin regeneration", Polym. Bull. 2013, 70:2337-2358, DOI 10.1007/s00289-013-0956-6.
Nagiah et al., "Highly Compliant Vascular Grafts with Gelatin-Sheathed Coaxially Structured Nanofibers", Langmuir 2015, vol. 31, pp. 12993-13002, DOI: 10.1021/acs.langmuir.5b03177.
Negut et al., "Scaffolds for Wound Healing Applications", Polymers 2020, Dec. 2010, pp. 1-19, doi: 10.3390/polym12092010.
Nemati et al., "Current progress in application of polymeric nanofibers to tissue engineering", Nano Convergence, (2019), 6:36, pp. 1-16, https://doi.org/10.1186/s40580-019-0209-y.
Ovsianikov et al., "Laser Fabrication of Three-Dimensional CAD Scaffolds from Photosensitive Gelatin for Applications in Tissue Engineering", Biomacromolecules, Dec. 2011, pp. 851-858.
Parotta et al., "Modeling Cardiac Disease Mechanisms Using Induced Pluripotent Stem Cell-Derived Cardiomyocytes: Progress, Promises and Challenges", International Journal of Molecular Sciences, Jun. 21, 2020, 4354; doi:10.3390/ijms21124354.

(56) References Cited

OTHER PUBLICATIONS

Petrosko et al, "Methods and Protocols", Methods Mol Biol, 2017, vol. 1570, pp. 261-278.

Politi et al, "Smart ECM-Based Electrospun Biomaterials for Skeletal Muscle Regeneration", Nanomaterials 2020, vol. 10:1781, pp. 1-19, doi:10.3390/nano10091781.

Ramalingam et al., "Poly-ϵ-Caprolactone/Gelatin Hybrid Electrospun Composite Nanofibrous Mats Containing Ultrasound Assisted Herbal Extract: Antimicrobial and Cell Proliferation Study", Nanomaterials, Sep. 2019, 462, pp. 1-21 doi:10.3390/nano9030462.

Sakai et al., "An injectable, in situ enzymatically gellable, gelatin derivative for drug delivery and tissue engineering", Biomaterials, 2009, 30, pp. 3371-3377.

Sensini et al., "Hierarchical electrospun tendon-ligament bioinspired scaffolds induce changes in fibroblasts morphology under static and dynamic conditions", Journal of Microscopy, 2019, vol. 277, Issue 3 2020, pp. 160-169.

Son et al., "Visible light-induced crosslinkable gelatin", Acta Biomaterialia 6 (2010), pp. 4005-4010.

Suh et al., "Electrospun Scaffolds and Induced Pluripotent Stem Cell-Derived Cardiomyocytes for Cardiac Tissue Engineering Applications", Bioengineering Jul. 2020, 105; pp. 1-21, doi:10.3390/bioengineering7030105.

Vats et al., "Embryonic stem cells and tissue engineering: delivering stem cells to the clinic", J R Soc Med, 2005, vol. 98, pp. 346-350.

Veldhuizen et al., "Three-dimensional microengineered models of human cardiac diseases", Journal of Biological Engerineering, 2019, 13:29, pp. 1-12, https://doi.org/10.1186/s13036-019-0155-6.

Venugopal et al, "Biomaterial strategies for alleviation of myocardial infarction", J. R. Soc. Interface, 2012, vol. 9, pp. 1-19, doi:10.1098/rsif.2011.0301.

Yarin, "Coaxial electrospinning and emulsion electrospinning of core-shell fibers", Polym. Adv. Technol, 2011, vol. 22, pp. 310-317.

Zhang et al, "Crosslinking of the electrospun gelatin nanofibers", Polymer, 2006, vol. 47, pp. 2911-2917.

Zhang et al, "Electrospinning of Gelatin Fibers and Gelatin/PCL Composite Fibrous Scaffolds", Wiley InterScience, 2004, pp. 156-165.

Zhang et al., "Fabrication of porous electrospun nanofibres", Nanotechnology, 2006, vol. 17, pp. 901-908.

Zhu et al., "In vivo engineered extracellular matrix scaffolds with instructive niches for oriented tissue regeneration", Nature Communications, Oct. 2019:4620, https://doi.org/10.1038/s41467-019-12545-3.

Zilla et al, "Prosthetic vascular grafts: Wrong models, wrong questions and no healing", Biomaterials, 2007, vol. 28, pp. 5009-5027.

Zong et al., "Electrospun fine-textured scaffolds for heart tissue constructs", Biomaterials, 2005, pp. 5330-5338.

* cited by examiner

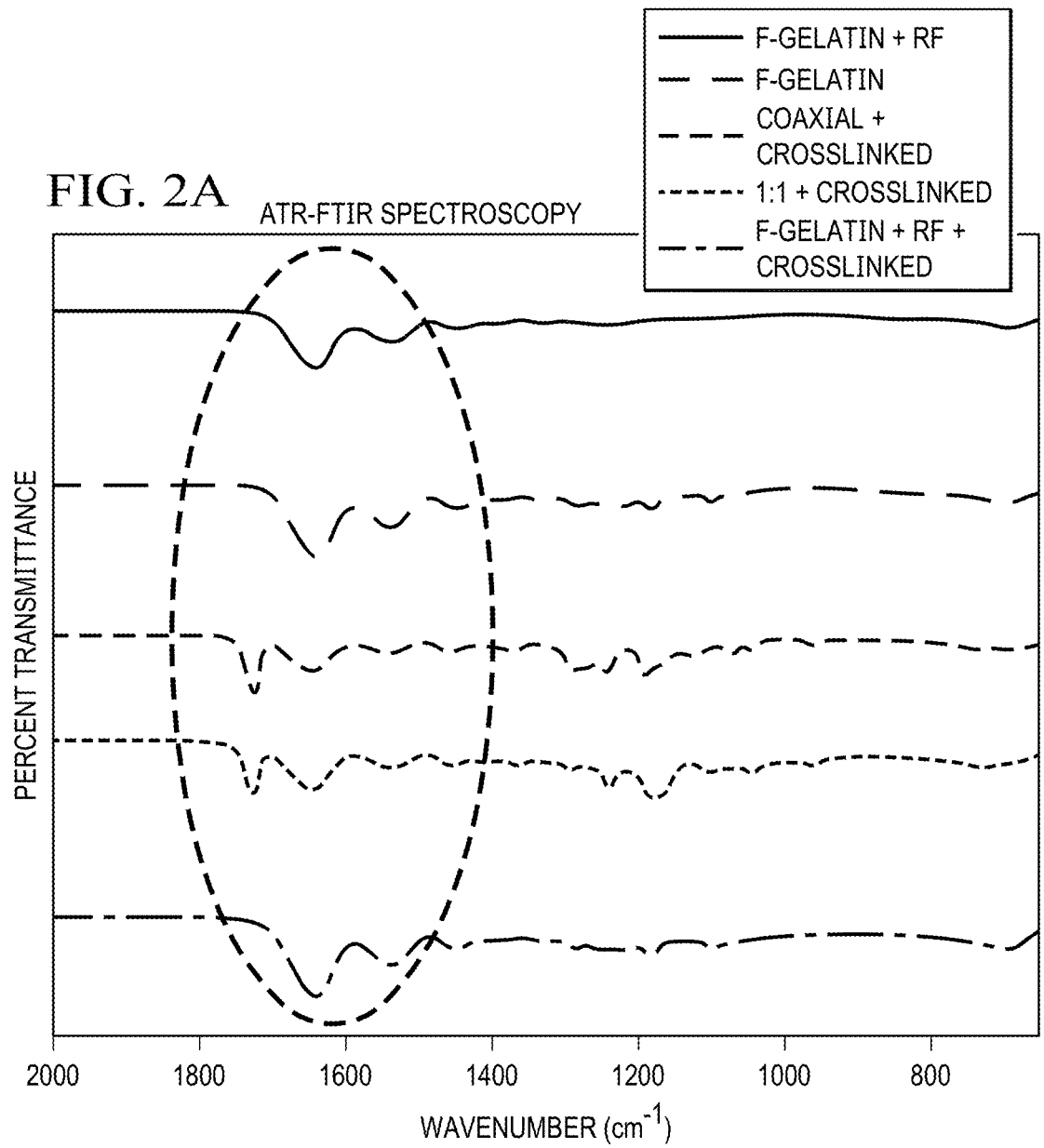

DEVELOPMENT AND CHARACTERIZATION OF F-GELATIN ELECTROSPUN SCAFFOLDS FOR CARDIAC TISSUE MODELING

CROSS-REFERENCE TO RELATED APPLICATION

This application is a utility conversion and claims priority to U.S. Application No. 63/364,834, filed May 17, 2022, the content of which is hereby incorporated herein by reference in its entirety for all purposes.

STATEMENT AS TO RIGHTS TO INVENTIONS MADE UNDER FEDERALLY-SPONSORED RESEARCH OR DEVELOPMENT

This invention was made with government support under grants #1828268 and #1927628 awarded by NSF; and grant #1SC1HL154511-01 awarded by NIH SC1. The government has certain rights in the invention.

BACKGROUND

Myocardial infarction (MI) is one of the leading causes of morbidity and mortality worldwide, which is caused by the irreversible death of cardiomyocytes in the heart wall. The loss of these terminally differentiated cardiomyocytes during MI leads to significant reduction in contractile efficiency after damage to the myocardium in the heart, subsequently leading to heart failure in the long term. The lack of reliable human model systems for studying cardiac diseases have posed as a severe challenge in the understanding of the molecular mechanisms and cellular processes during the progression of heart disease. Studies have attempted to model cardiac tissues through traditional tissue engineering approaches to understand heart diseases at their initial stage. One of the major goals in tissue engineering involves the development of ideal scaffolds for regenerating damaged tissue/organ. Nanofibrous scaffolds serve as suitable environment for cell attachment and proliferation due to similarity with natural extracellular matrix (ECM). However traditional scaffolds often have inherently low mechanical and handling properties which poses as a disadvantage. Electrospinning is a simple and versatile method for generating nanofibers from a variety of materials that include polymers, composites, and ceramics. Electrospun fibrous scaffolds with high surface area to volume ratio and superior mechanical properties have been applied in wound healing, tissue engineering, and drug delivery. Moreover, ECM mimicking constructs laden with stem cells bear promise towards in vivo transplantation as they reduce the probability of an immune response since the cells are obtained autologously from patients.

Our goal in this study was to develop a set of furfuryl-gelatin (f-gelatin) based electrospun scaffolds for modelling of cardiac tissues. Gelatin is most favored for the preparation of cell based scaffolds in tissue engineering on account of its biodegradability, enhanced cell binding ability due to the presence of an RGD-(Arg-Gly-Asp)-sequence and its widespread availability at a low cost. Moreover, its lower immunogenicity and its ability to be modified with the inclusion of other materials in order to significantly alter its biochemical properties while enhancing its mechanical properties make it an ideal polymer biomaterial for applications in tissue engineering and regenerative medicine. Crosslinking of gelatin enzymatically or with chemical agents like glutaraldehyde usually render the resultant compound toxic. In order to overcome this drawback, Son et al. developed visible-light crosslinkable gelatin by the introduction of furfuryl groups. We had previously adopted this f-gelatin for the biofabrication of scaffolds to study the interactions between STO fibroblasts and C2C12 over a sustained period. However, the rheological analysis performed on the aforementioned scaffolds revealed an elastic modulus of 1.7 kPa, which is significantly lower than that of the native ECM present in the myocardium. Hence a platform with an elastic modulus closely mimicking the mechanical properties of the native heart tissue needs to be developed to serve as a scaffold for cardiac tissue model. Thus, we hypothesized that blending of the hydrophilic f-gelatin with the hydrophobic polymer polycaprolactone (PCL) will enhance the elastic modulus of the resultant scaffolds in order to be used as platforms for modeling of cardiac tissues. PCL is an optimal hydrophobic biodegradable polymer which has been used as a component for making cardiac tissue scaffolds. In spite of the high mechanical stability of PCL, it lacks the innate reactive sites for cell adhesion. The hydrophobic nature of PCL also tends to attract platelet and plasma protein adhesion, leading to a prolonged inflammatory response from the host. Hence, we postulated that combining PCL with f-gelatin would ensure that the hydrophobic PCL provides the mechanical strength and stability of the scaffold, while the f-gelatin would enhance biocompatibility to mimic the ECM properties of native biological tissue.

In this study, we developed four types of electrospun scaffolds based on f-gelatin including 1) f-gelatin electrospun scaffolds; 2) f-gelatin with PCL in the ratio of 1:1; 3) coaxial PCL (polycaprolactone core: inside) with f-gelatin (sheath: outside) (coaxial f-gelatin>PCL); 4) PCL electrospun scaffolds coated with Corning Matrigel Matrix were developed through single nozzle electrospinning and coaxial electrospinning, respectively. To our knowledge, this is the first study reporting the development and establishment of f-gelatin based scaffolds via electrospinning. The physical, mechanical, and biological performance of these hybrid nanofibrous scaffolds as platforms for growing cardiac cells were evaluated in this study. The electrospinning parameters were optimized for all three scaffolds and their structural and mechanical integrity were characterized through electron microscopy and rheological studies. The interaction between the blended electrospun scaffolds (f-gelatin with PCL 1:1, coaxial f-gelatin>PCL) were assessed through thermal analysis and Attenuated Total Reflection-Fourier Transformed Infrared (ATR-FTIR) spectroscopy. The biodegradation behavior of all scaffolds was analyzed through swelling studies accompanied by scanning electron microcopy (SEM). The biocompatibility of all the electrospun scaffolds were analyzed for a period of 1-week with human AC16 cardiomyocytes. The biocompatibility of the coaxial f-gelatin>PCL scaffolds with an expected higher elastic modulus was assessed further through adhesion and functionality of hiPSC derived cardiomyocytes thereby confirming the potential of the scaffolds as an ideal platform for developing cardiac tissue-on-a-chip models. The results obtained can support the use of these electrospun scaffolds in-vitro preclinical platforms for modeling healthy and diseased cardiac tissue states beneficial for drug screening or regenerative engineering applications. This study collectively demonstrates a facile approach to produce visible light crosslinkable, hybrid, biodegradable nanofibrous scaffold biomaterials which can be adopted as versatile cardiac tissue engineering platforms.

SUMMARY

Scanning electron microscopy revealed uniform fibrous structures in scaffolds with significantly varying average fiber diameters of 760±80 nm (f-gelatin), 420±110 nm (f-gelatin and PCL (1:1)), and 810±60 nm (coaxial f-gelatin>PCL)respectively. Transmission electron microscopy further displayed the core-sheath structures of the coaxial f-gelatin>PCL electrospun fibrous scaffolds. Thermal analysis and Attenuated Total Reflection-Fourier Transformed Infrared (ATR-FTIR) spectroscopy revealed no interactions between the polymers in the blended electrospun scaffolds. The varied blending methods led to significant differences in the elastic moduli of the electrospun scaffolds with the coaxial f-gelatin>PCL revealing the highest elastic modulus of all scaffolds (164±3.85 kPa). All scaffolds exhibited excellent biocompatibility by supporting the adhesion and proliferation of human AC16 cardiomyocytes cells. The biocompatibility of the coaxial f-gelatin>PCL scaffolds with superior elastic modulus was assessed further through adhesion and functionality of human induced pluripotent stem cell (hiPSC)-derived cardiomyocytes thereby confirming the potential of the coaxially spun scaffolds as an ideal platform for developing cardiac tissue-on-a-chip models. Our results demonstrate a facile approach to produce visible light cross linkable hybrid, biodegradable nanofibrous scaffold biomaterials which can be adopted as platforms for cardiac tissue engineered models.

There is a need for the following embodiments of the present disclosure. Of course, the present disclosure is not limited to these embodiments.

According to an embodiment of the present disclosure, a composition of matter comprises: furfuryl amine-conjugated gelatin; a solvent; and a biocompatible biodegradable crosslinking photo initiator. The biocompatible biodegradable crosslinking photo initiator can include a biocompatible biodegradable visible light crosslinking photo initiator that includes riboflavin.

According to another embodiment of the present disclosure, a method of making nanofibrous scaffold biomaterials, comprises: providing a polymer solution comprising furfuryl amine-conjugated gelatin; a solvent; and a biocompatible biodegradable crosslinking photo initiator; and electrospinning the polymer solution to form cross linkable electrospun nanofibers. Electrospinning can include coaxial electrospinning and the method can further comprise exposing the electrospun polymer solution to visible light after electrospinning.

These, and other, embodiments of the present disclosure will be better appreciated and understood when considered in conjunction with the following description and the accompanying drawings. It should be understood, however, that the following description, while indicating various embodiments of the present disclosure and numerous specific details thereof, is given for the purpose of illustration and does not imply limitation. Many substitutions, modifications, additions and/or rearrangements may be made within the scope of embodiments of the present disclosure, and embodiments of the present disclosure include all such substitutions, modifications, additions and/or rearrangements.

BRIEF DESCRIPTION OF THE DRAWINGS

The drawings accompanying and forming part of this specification are included to depict certain embodiments of the present disclosure. A clearer concept of the embodiments described in this application will be readily apparent by referring to the exemplary, and therefore nonlimiting, embodiments illustrated in the drawings (wherein identical reference numerals (if they occur in more than one view) designate the same elements). The described embodiments may be better understood by reference to one or more of these drawings in combination with the following description. It should be noted that the features illustrated in the drawings are not necessarily drawn to scale.

FIG. 2A-2B illustrate ATR-FTIR spectroscopy of different electrospun scaffolds.

DETAILED DESCRIPTION

Chemicals

Figure 1A:
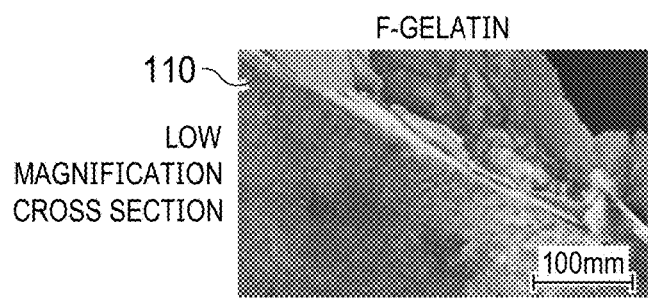
FIGS. 1A-1M are: A-C SEM images of cross-section of f-gelatin; f-gelatin and PCL (1:1) and coaxial f-gelatin>PCL electrospun scaffolds (Scale bar 1 mm); D-F SEM images of cross-section of f-gelatin; f-gelatin and PCL (1:1) and coaxial f-gelatin>PCL electrospun scaffolds (Scale bar 100 µm); G-I SEM images of cross-section of f-gelatin; f-gelatin and PCL (1:1) and coaxial f-gelatin>PCL electrospun scaffolds (Scale bar 20 µm); J TEM image of Coaxial f-gelatin>PCL electrospun scaffolds (Scale bar 100 nm); K SEM image of cross-section of f-gel electrospun scaffold (Scale bar 50 µm); and L-M SEM images of PCL>Matrigel Coating electrospun scaffold surface (Scale bar 100 um).

Furfuryl-gelatin or f-gelatin was prepared by homogeneous addition of furfuryl glycidyl ether to a porcine gelatin solution. Phosphate Buffered Saline 10× Solution and 1,1,1,3,3,3 hexafluoroisopropanol (HFP) were purchased from Fisher Bioreagents, USA. Polycaprolactone (PCL) of average Mn 80,000 was purchased from Sigma Aldrich, St Louis, MO, USA.

Cell Studies

Two different cardiac cell types were utilized for this study. Human AC16 cardiomyocytes cell lines and Cellartis human iPSC derived cardiomyocytes were utilized to determine the biocompatibility of the electrospun scaffolds. The Cellartis cardiomyocytes were adopted due to their properties that render them uniquely qualified as model systems for studying human diseases like cardiomyopathies, rhythm disorders, valvular, vascular disorders, and metabolic risk factors for ischemic heart disease. The AC16 human cardiomyocyte cell lines (SCC109, EMD Millipore, MA, USA) were cultured and expanded in Dulbecco's Modified Eagle Medium (DMEM/F12; Sigma Cat. No. D6434) containing 2 mM L-Glutamine (EMD Millipore Cat. No. TMS-002-C), 10% FBS (EMD Millipore Cat. No. ES-009-B) and 1× Penicillin-Streptomycin Solution (EMD Millipore Cat. No. TMS-AB2-C). PKH26 Red Fluorescent Cell Linker Mini Kit (Sigma Aldrich, MO, USA), and DAPI (Thermo Fisher Scientific, USA) were used as cell labeling dyes. In addition, 48 and 24-well flat-bottom plates (Thermo Fisher Scientific, USA) were used for in vitro cultures. Trypsin-Ethylenediaminetetraacetic acid (EDTA, 0.25%, phenol red, ThermoFisher) was used for cell detachment. PCL scaffolds were covered with Matrigel (Corning Matrigel Matrix Cat. No. 356237) purchased from Corning Inc., Corning, NY, USA.

Cellartis Cardiomyocytes (from ChiPSC22; Cat No. Y10076) are human cardiomyocytes derived from induced pluripotent stem cells (iPSCs) and were obtained from Takara Bio, USA. These cells were cultured in Cellartis culture base (Cat No. Y10063) with 10% FBS and stabilized prior to experiment. Both AC16 human cardiomyocytes and Cellartis Cardiomyocytes were stained with PKH26 dye (Sigma Aldrich, St. Louis, MO) prior to seeding on electrospun scaffolds as per manufacturer recommendations.

Synthesis of f-Gelatin

F-gelatin was synthesized and characterized. Briefly, porcine gelatin (2 g) was dissolved in double distilled water (80 mL) and 1N NaOH solution was added to adjust the pH to 11. Furfuryl glycidyl ether (250 µL) was dissolved in DMSO (20 mL) and added to the gelatin solution at room temperature following which the mixture was stirred for 30 h at 65° C. The resulting mixture was adjusted to pH 7 by the addition of 1N HCl solution and dialyzed in deionized (DI) water for 48 h to purify the f-gelatin using a dialysis membrane with a molecular weight cut-off of 1000 Da (Spectrum Laboratories Inc., Rancho Dominguez, CA). Following dialysis, the solution was evaporated, and the purified f-gelatin was first washed four times with acetone, once with ether and then dried. The dried f-gelatin was used for further studies.

Electrospinning of f-Gelatin Based Scaffolds

The apparatus used for obtaining coaxial fibers was developed in-house. F-gelatin polymer solutions of 10% w/v concentration were prepared by dissolving 1 g of dried f-gelatin in 10 mL of 1,1,1,3,3,3 HFP. The visible light crosslinking photo initiator, riboflavin (RF) was procured from ThermoFisher Scientific (Waltham, MA). 100 µL of RF (5% w/v in 1, 1, 1,3,3,3 hexafluoro-2-propanol) was added to the f-gelatin solution. Blended polymer solutions of 10% w/v were obtained by individually dissolving 5% w/v of dried f-gelatin and 5% w/v of PCL in 10 mL of 1, 1, 1,3,3,3 hexafluoro-2-propanol. The dissolved solutions were further mixed and after stirred for 6-8 h to obtain blended solution of PCL and f-gelatin in the ratio of 1:1. The polymer solutions were then loaded in 5 mL syringes with 24 G needle connected to the positive terminal of a high voltage DC supply (ES30P 10 W power supply, Gamma High Voltage Research, Ormond Beach, FL). In case of coaxial electrospinning, the polymer solutions were loaded in different syringes. PCL solution was passed through an inner needle of 22 G (0.71 mm internal diameter) and the sheath f-gelatin solution was passed through the outer needle of 16 G (1.65 mm internal diameter). The RF solution was added to the f-gelatin solutions before electrospinning. The fibers were deposited onto a grounded aluminum substrate placed at a distance of 10 cm perpendicular to the needle. Fibers were electrospun at room temperature (26° C.) and a relative humidity of 78%. The resulting electrospun fibers were then crosslinked by immediately exposing to visible light for 2 min (400 nm wavelengths at 100% intensity, Intelli-Ray 600, Uvitron International, West Springfield, MA). After the cross-linking process, the electrospun scaffolds were rinsed with phosphate buffered saline (pH 7.4) and used for further studies. Rinsing at least a portion of the polymer solution after exposing helps to stabilize the samples. The obtained samples were stored at room temperature until further use.

Electrospinning of PCL Based Scaffolds

The apparatus used for obtaining PCL fibers was developed in-house. 0.05% w/v PCL polymer solution was obtained by weighting of 1.425 g of PCL and dissolving it in 25.20 mL HFP (0.25:3 ratio). Dissolved solution was mixed with a magnetic stirrer for 6-8 h until a homogeneous mixture was obtained. The polymer solution was then loaded in 10 mL syringes with 22 G needle connected to the positive terminal of a high voltage DC supply (ES30P 10 W power supply, Gamma High Voltage Research, Ormond Beach, FL). The fibers were deposited onto a grounded aluminum rotating collector placed at a distance of 15 cm perpendicular to the needle Fibers were electrospun at room temperature (26° C.) and a relative humidity of 72%, with current of 0.03 mA, voltage of 18 kV, during periods of 15-30 min of deposition. After the electrospinning process, the electrospun scaffolds were rinsed with phosphate buffered saline (pH 7.4), left to dry overnight (12 h), and used for further studies. Rinsing at least a portion of the polymer solution after exposing helps to stabilize the samples. The obtained samples were stored at room temperature until further use.

Matrigel Coating Solution Preparation

Matrigel solution was thawed at 4° C. for 2 hrs. Pipette tips were maintained at 4° C. a to keep them cold, as well as growth media (with no FBS). All tools and main components were placed on ice and subsequently placed on the biosafety cabinet. Everything was done quickly to prevent Matrigel's viscosity from increasing (behave more solid like). With a pipette, 1 mL of growth media was placed on a new conical tube and 50 µL of Matrigel was added, followed by resuspension. The new coating solution was placed and utilized on ice.

PCL Scaffolds Coated with Matrigel

After preparing Matrigel coating solution, 19.1 mm circular PCL scaffolds were coated with 500 µL (0.5 ml) of Matrigel solution in a 12-well plate that was subsequently placed in a belly dancer for 5 minutes, which will help achieve an even distribution of the solution throughout the surface of the scaffold. Posteriorly, the plate was placed in the incubator at 37° C. for 1 hr and the residual liquid was removed from each of the wells.

Characterization of the Electrospun Fibers

The physiochemical characterization of the scaffolds was performed to analyze and choose an optimal scaffold as potential platforms for cardiac tissue modeling. The exposed polymer solution including the biocompatible biodegradable crosslinking photo initiator are the basis for embodiment of this disclosure.

Scanning Electron Microscopy (SEM)

SEM was performed to analyze the surface morphology of the electrospun scaffolds. The samples were mounted on brass stubs and were sputter-coated with gold/palladium (2-3 min) in a sputter coater (Gatan Model 682 Precision etching coating system, Pleasantown, CA, USA) and visualized using SEM (S-4800, Hitachi, Japan) at 7 kV voltage and current of 5 µA at varying magnifications. The samples were mounted on aluminum stubs and were sputter-coated with gold (30 sec) in plasma sputter coater (JEOL Smart Coater, JEOL USA, Inc. Peabody, MA, USA) and visualized using SEM (SU-3500, Hitachi, Japan) at 10 kv and current of 0.114 µA at varying magnifications, SEM (TM-1000, Hitachi, Japan) at 15 kV and 33.2 mA at varying magnifications. The diameters of about 50 different fiber samples were measured in each sample group using Image J to obtain their average diameter.

Transmission Electron Spectroscopy (TEM)

TEM was performed on coaxial f-gelatin>PCL electrospun scaffolds using an H7650 TEM (Hitachi Ltd., Tokyo, Japan) operating at 80 kV to analyze its internal structure as it cannot be revealed using SEM. The electrospun fiber samples for TEM observation were prepared by directly depositing the as-spun fibers on formvar coated Cu TEM grids (Ted Pella Inc, Redding, CA, USA. Catalog No. 01700-F, USA).

Attenuated Total Reflection-Fourier Transform Infrared Spectroscopy (ATR-FTIR)

ATR-FTIR was performed on the electrospun scaffolds to analyze interaction between the blended polymers during the electrospinning process. Measurements were carried out on the fibrous scaffolds using a Thermo Mattison spectrometer (Thermo Mattison, Waltham, MA,) equipped with a ZnSe ATR crystal. Typically, 32 scans were signal-averaged to reduce spectral noise. The spectrum of the samples was recorded from 400 to 4000 $cm^{-1}$ to assess the interaction between the polymers. The peaks match the reference's peaks a 93.72% according to the report results, other databases matched between 80-90%. The main peaks can be found between 2800-3000 $cm^{-1}$ indicating the C—H functional group in CH2, and ranges between 1600-1800 $cm^{-1}$ indicating Carboxyl functional groups. These results confirm the molecular arrangement of PCL electrospun fibers. The PCL/Matrigel absorbance plot shows extra peaks 1500-1700 $cm^{-1}$ that are not found in PCL material. Both of peaks are indicators of the main protein content of Matrigel which are collagen and laminin. The first peak shown in the graph are amides expressing chemically in the film. To confirm that gelatin (collagen) is present, F-gel and PCL/Matrigel scaffolds were compared, and peaks are present around the same ranges.

Thermal Analysis (Thermogravimetric (TGA) Analysis and Differential Scanning Calorimetry (DSC))

Thermal analysis was performed to elucidate the thermal stability of electrospun scaffolds and further discern the interaction or lack of interaction between the blended polymer systems. TGA of the fibers was performed using a universal Mettler TGA Analyzer, Model TGA/DSC 1 (Mettler-Toledo, Columbus, OH). About 5 mg of the samples was heated at 10° C. $minute^{-1}$ in a temperature range of 0-600° C. using platinum crucibles. DSC analysis of the fibers was performed from 0-300° C. at 10° C. $minute^{-1}$ using Mettler TGA Analyzer, Model TGA/DSC 1. The instrument was calibrated using an indium standard, and the calorimeter cell was flushed with liquid nitrogen at 20 mL $minute^{-1}$.

Rheological Analysis

The elastic modulus of the electrospun scaffolds were elucidated by studying their rheological properties. To examine the rheological properties of the electrospun scaffold the samples were soaked in 1×PBS for 24 hours before testing. Oscillatory shear stress rheometric study was performed using an Anton-Paar MCR 92 rheometer (Anton-Paar, Austria) with a PP25/S measuring system at 1% strain with a frequency range between 0.5 and 50 Hz. Analysis for frequency and strain was conducted within the viscoelastic range of the samples. Storage/Loss moduli, complex viscosity and elastic modulus were measured at 1.99 Hz as previously done and reported.

Hydrophilicity Analysis by Measuring Contact Angle

Prior to performing degradation studies, the hydrophilicity of all samples was determined using contact angle measurement with a semi-professional camera (Canon EOS Rebel T8i EF-S 18-55 mm) was used to capture a slow-motion video of a drop of water touching the surface. This procedure was repeated three times on each sample and contact angle measurements were taken using Image J. After measurements, an average contact angle was calculated for each surface. Contact angle measurements classified surfaces as hydrophilic for angles lower than 90 degrees ($\theta<90°$) and hydrophobic for angles greater than 90 degrees ($\theta>90°$). F-gelatin coating, the contact angle on the surface is 54.38°; PCL electrospun fibers have an average contact angle on the surface is 112.13° degrees; PCL>Matrigel electrospun fibers have an average contact angle on the surface of 46.99° degrees. Evaluating a significant reduction in contact angle in PCL scaffolds when it is coated with Matrigel. v Swelling and Morphological Analysis of Electrospun Scaffolds Degradation studies were performed on electrospun scaffolds to assess their structural stability during long term in vitro studies. The cross linked electrospun scaffolds were cut into dimensions of 2×2 $cm^2$ for in vitro degradation studies. The cut specimens were placed in petri plates containing DMEM/F12 with 2 mM L-Glutamine, 10% FBS and 1× Penicillin-Streptomycin Solution at 37° C. humidified with 5% $CO_2$ for 14 and 21 days, respectively. The specimens were recovered at the end of each degradation period and were analyzed using SEM.

Biological Assessment of the Electrospun Scaffolds

The biological assessment of the scaffolds was performed to analyze and choose the optimal scaffold as potential platforms for cardiac tissue modeling. MTS assay was also performed to evaluate cell viability and proliferation at day 0 and day 3 after incubation. The MTS assay protocol is based on the reduction of the MTS tetrazolium compound to generate a colored formazan dye that is soluble in cell culture media, that was then further analyzed with a plate reader.

Human AC16 Cardiomyocytes Cell Culture and Adhesion on Electrospun Scaffolds

AC16 cardiomyocytes were pre-stained using the PKH26 cytoplasmic staining dye and seeded on the fibrous scaffolds placed in a 24-well culture plate (Corning, NY, USA) and maintained in DMEM/F12 containing 2 mM L-Glutamine, 10% FBS and 1× Penicillin-Streptomycin Solution at 37° C. humidified with 5% $CO_2$. The cell seeding density was 25,000 cells/$cm^2$ on scaffolds each approximately 1.9 $cm^2$ in area that was designed to fit within the 24 wells. After 24 h of culture, the cell-laden constructs were fixed using 4%

PFA and mounted on glass slides and imaged using a confocal fluorescence microscope (Olympus IX81 inverted fluorescence motorized microscope, Japan) to confirm the adhesion and retention of viable cells on the electrospun scaffolds.

Flow Cytometry Analysis (FACS)

To estimate cell proliferation and overall biocompatibility of the electrospun scaffolds, the AC16 human cardiomyocytes were prestained using Cell Trace Violet, proliferation kit (Invitrogen, Carlsbad, CA) using manufacturer's protocols, for this experiment. These prestained cells were seeded on the electrospun scaffolds (25,000 cells/cm$^2$ on a total area of 1.9 cm$^2$) and cultured for 24 h and 7-days, respectively (37° C., 5% $CO_2$). After 24 h and 7 days, cells on the electrospun scaffolds were treated using Trypsin-EDTA (0.25%, phenol red), to detach and extract the cells for FACS analysis. Extracted cells were fixed with 4% PFA for 15 min at room temperature and added to their designated FACS analysis falcon tubes and analyzed using Beckman Coulter Gallios Flow Cytometer (Brea, CA, USA) using excitation and emission wavelengths of 405 and 450 nm respectively after 24 h and 7 days. Positive controls included pre-stained cells grown on plastic petri dishes for 48 h. Negative controls included non-stained cells grown on plastic petri dishes for 48 h.

Culture of Human hiPSC Derived Cardiomyocytes

Based on the expected superior mechanical properties of the coaxial f-gelatin>PCL electrospun scaffolds, they were chosen for further studies with human hiPSC derived cardiomyocytes for developing a cardiac tissue model. Cellartis cardiomyocytes (10,000 cells/0.95 cm$^2$) were seeded on coaxial f-gelatin>PCL scaffolds placed in 48 well plates and cultured in Cellartis culture base with 10% FBS at 37° C. humidified with 5% $CO_2$. After 48 h of culture, the cell-laden constructs were fixed using 4% PFA and mounted on glass slides and imaged using a confocal fluorescence microscope (Olympus IX81 inverted fluorescence motorized microscope, Japan) to confirm the adhesion and retention of cells on the electrospun scaffolds.

Statistical Analysis

All experiments were performed in triplicate and numerical data are reported as mean±standard deviation. All data were compared using ANOVA with $p<0.05$ considered to be statistically significant.

Morphological and Structural Analysis of the Electrospun Scaffolds

SEM images of the crosslinked electrospun samples are shown in FIGS. 1A-1J. Well-formed robust fibers were observed in all electrospun scaffolds and their average fiber diameters are tabulated in Table 1.

Figure 1B:
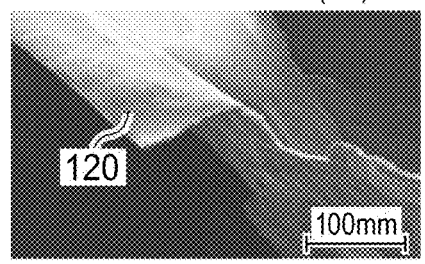
Figure 1C:
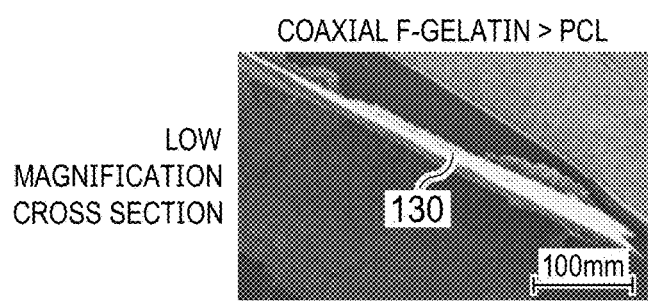
Figure 1D:
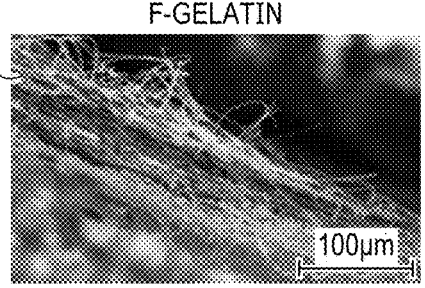
Figure 1E:
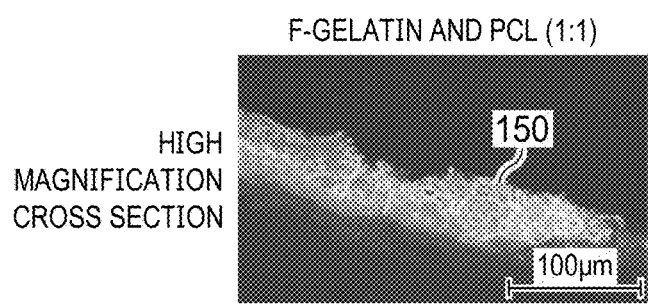
Figure 1F:
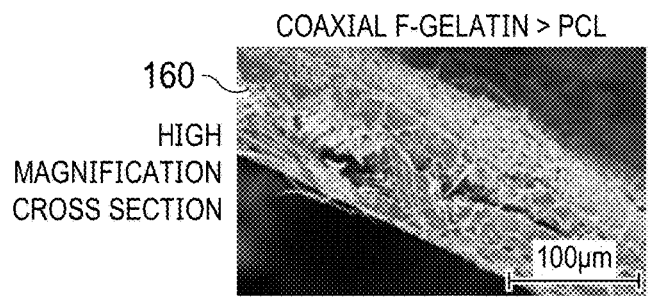
Figure 1G:
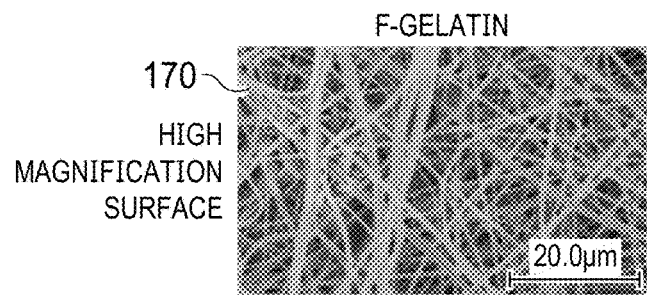
Figure 1H:
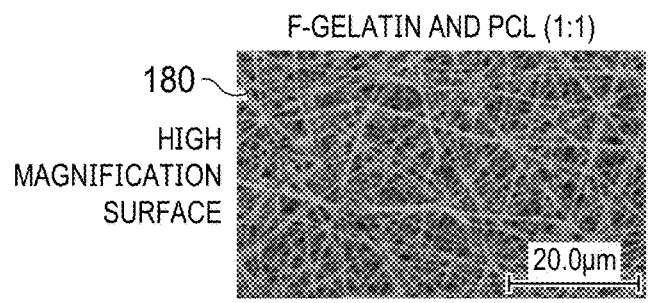
Figure 1I:
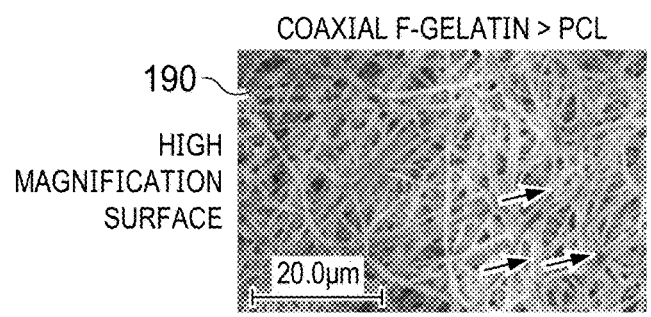
Figure 1J:
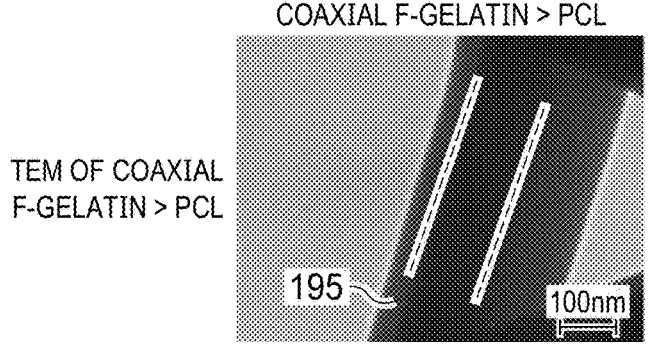
Figure 1K:
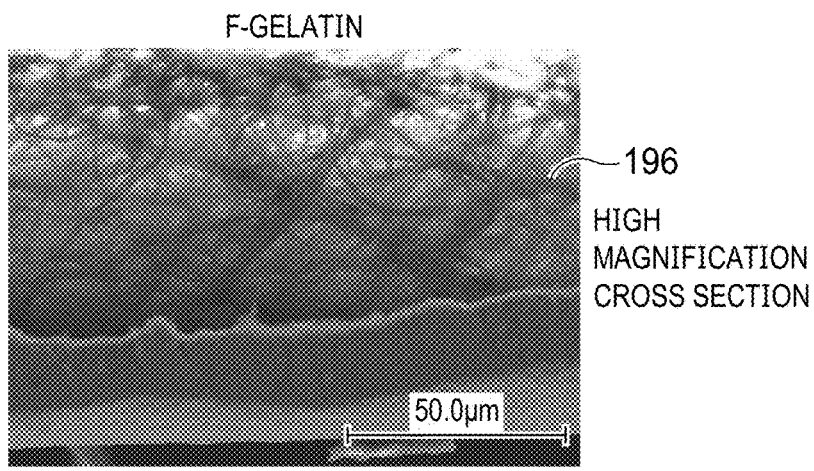
Figure 1L:
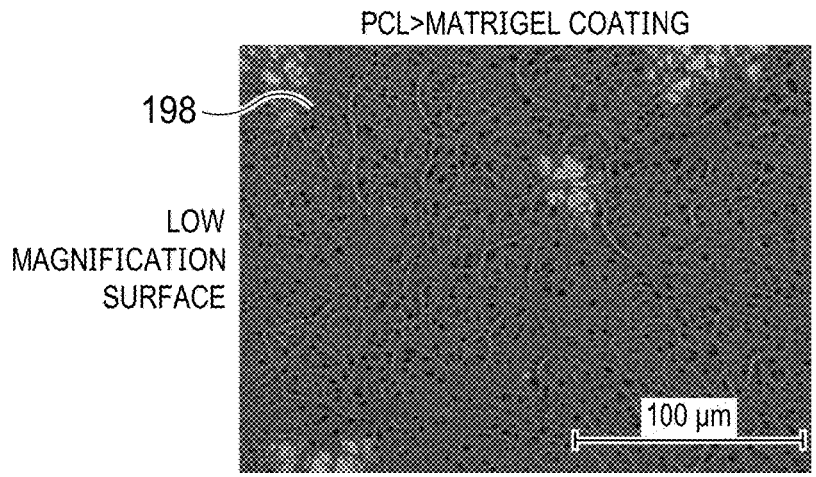
Figure 1M:
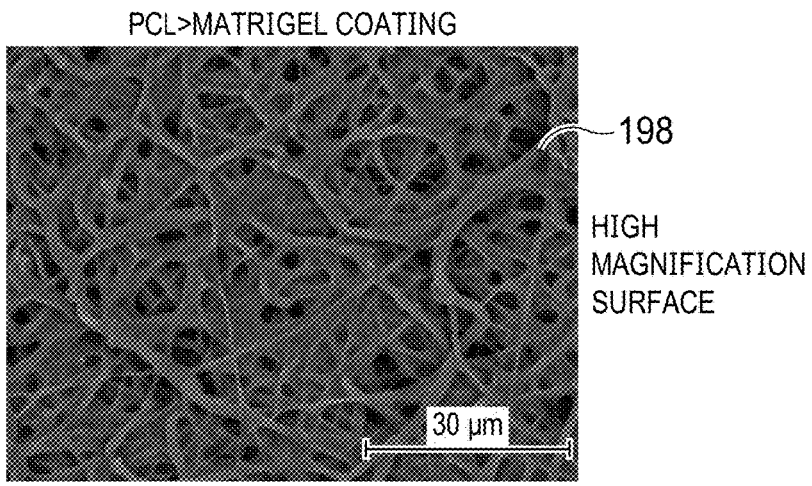

FIGS. 1A-1M show cross-sectional images of the electrospun scaffolds in low (FIGS. 1A-1C) and high magnification (FIGS. 1D-1M) respectively. FIG. 1A shows a low magnification cross of f-gelatin 110. FIG. 1B shows a low magnification cross section of 1:1 f-gelatin and PCL 120. FIG. 1C shows a low magnification cross section of coaxial f-gelatin over PCL 130. FIG. 1D shows a high magnification cross section of f-gelatin 140. FIG. 1E shows a high magnification cross section of 1:1 f-gelatin and PCL 150. FIG. 1F shows a high magnification cross section of coaxial F gelatin over PCL 160. FIG. 1G shows a high magnification surface image of f-gelatin 170. FIG. 1H Shows a high magnification surface image of 1:1 f-gelatin and PCL 180. FIG. 1I shows a high magnification surface image of coaxial f-gelatin over PCL 190. FIG. 1J shows a transmitting electron micrograph of coaxial f-gelatin over PCL 195. the furfuryl amine-conjugated gelatin is connected to and coats the polycaprolactone to define a coaxial scaffold having a polycaprolactone core and a furfuryl amine-conjugated gelatin sheath. FIG. 1K shows an SEM image of cross-section of f-gel electrospun scaffold 196 (Scale bar 50 μm). FIG. 1L shows an SEM images of PCL>Matrigel Coating electrospun scaffold surface 198 (Scale bar 100 um). FIG. 1M shows an SEM images of PCL>Matrigel Coating electrospun scaffold surface 198 (Scale bar 30 um).

Figure 9A:
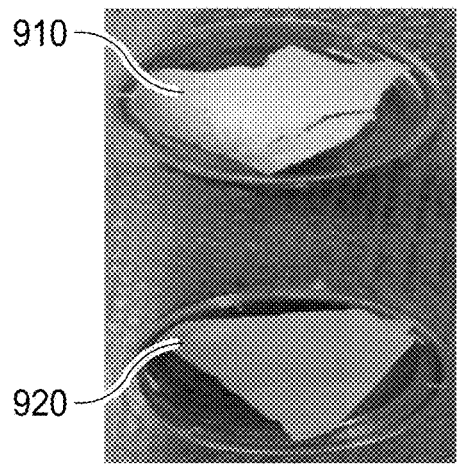
FIGS. 9A-9C are: A image of uncross linked(top) and crosslinked f-gel electrospun fibers; B free standing crosslinked f-gel electrospun fibers; and C translucent nature of f-gel fiber when wet.
Figure 9B:
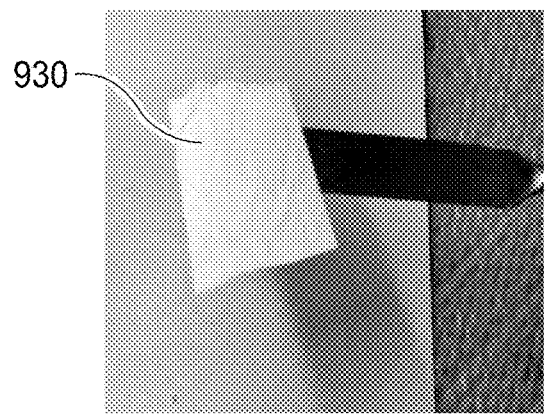
Figure 9C:
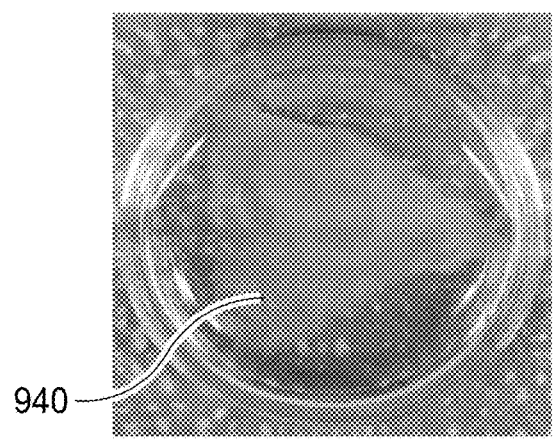

The thickness of the electrospun scaffolds varied between 50-75 μm and were used as such for characterization of the scaffolds. The yellow color present in the non-crosslinked scaffolds was due to the presence of riboflavin (RF) which was used as an initiator for visible light crosslinking (FIGS. 9A-9C). FIG. 9A shows an un-crosslinked f-gelatin electrospun fiber structure 910 and a crosslinked f-gelatin electrospun fiber structure 920. FIG. 9B shows a free standing crosslinked f-gelatin electrospun structure 930. FIG. 9C shows the translucent nature of f-gelatin electrospun fiber 940 when wet.

The fading of the yellow color confirmed the completion of the photo-crosslinking process (optimized in our laboratory: results not included) in all the electrospun scaffolds. The average diameter of the blended f-gelatin and PCL (1:1) scaffolds was found to be the lowest (420±110 nm) and it was noted to be the highest (810±60 nm) for the blended coaxial f-gelatin>PCL electrospun scaffolds. The optimized parameters for electrospinning, as tabulated in Table 1 outlines that the distance between the tip and collector, the accelerating voltage and total concentration of the polymer solutions were all maintained constant. Hence, the significant change in average fiber diameters were due to the flow rate and addition of PCL in samples containing the latter. Viscosity of the polymer solutions influences the average

TABLE 1

Optimized parameter for electrospinning f-gelatin based fibers

| Scaffold type | F-gel | F-gelatin and PCL (1:1) | Coaxial f-gelatin > PCL |
|---|---|---|---|
| Concentration of polymer(s) | 10% w/v (f-gel) | 5% w/v (f-gel) 5% w/v (PCL) | 5% w/v (f-gel) 5% w/v (PCL) |
| Solvent | 1,1,1,3,3,3 HFP | 1,1,1,3,3,3 HFP | 1,1,1,3,3,3 HFP |
| Flow rate | 0.5 mL/h | 1 mL/h | Core-0.5 mL/h Sheath- 0.5 mL/h |
| Accelerating voltage | 1.5 kV/cm | 1.5 kV/cm | 1.5 kV/cm |
| Distance between tip and collector | 10 cm | 10 cm | 10 cm |
| Average fiber diameter (nm) | 760 ± 80 nm | 420 ± 110 nm | 810 ± 60 nm | fiber diameters of the electrospun scaffolds in a proportional manner. Hence, the significant difference in the scaffold diameters was due to the lowering of the viscosity (results not included). In case of the coaxially spun f-gelatin>PCL scaffolds, the polymer solutions were not blended conventionally thereby leading to a corresponding increase in average fiber diameter.

Coalescence of fiber-junctions was found to be predominant in coaxial f-gelatin>PCL electrospun scaffolds (red arrows in FIG. 1I). During coaxial electrospinning, the evaporation of the core polymer solvent occurs through the sheath. The latent evaporation of the core solvent through the sheath led to formation of coalescent junctions in coaxial f-gelatin>PCL electrospun scaffolds. Coalescence at fiber-junctions in coaxial f-gelatin>PCL electrospun scaffolds are advantageous as they enhance the elastic modulus of the scaffolds. FIG. 1J represents a TEM image of the coaxial f-gelatin>PCL electrospun scaffolds, that clearly indicates the core-shell structure of the coaxial f-gelatin>PCL fibers. The core diameter of the coaxial f-gelatin>PCL fibers was found to be significantly lower in comparison with the sheath diameter (p=0.03). Since the PCL polymer solution (core) had significantly lower viscosity when compared to the f-gelatin (sheath) polymer solution, this resulted in higher diameter of the sheath.

Thermal Stability and Interaction of the Polymers in the Electrospun Scaffolds

Figure 2B:
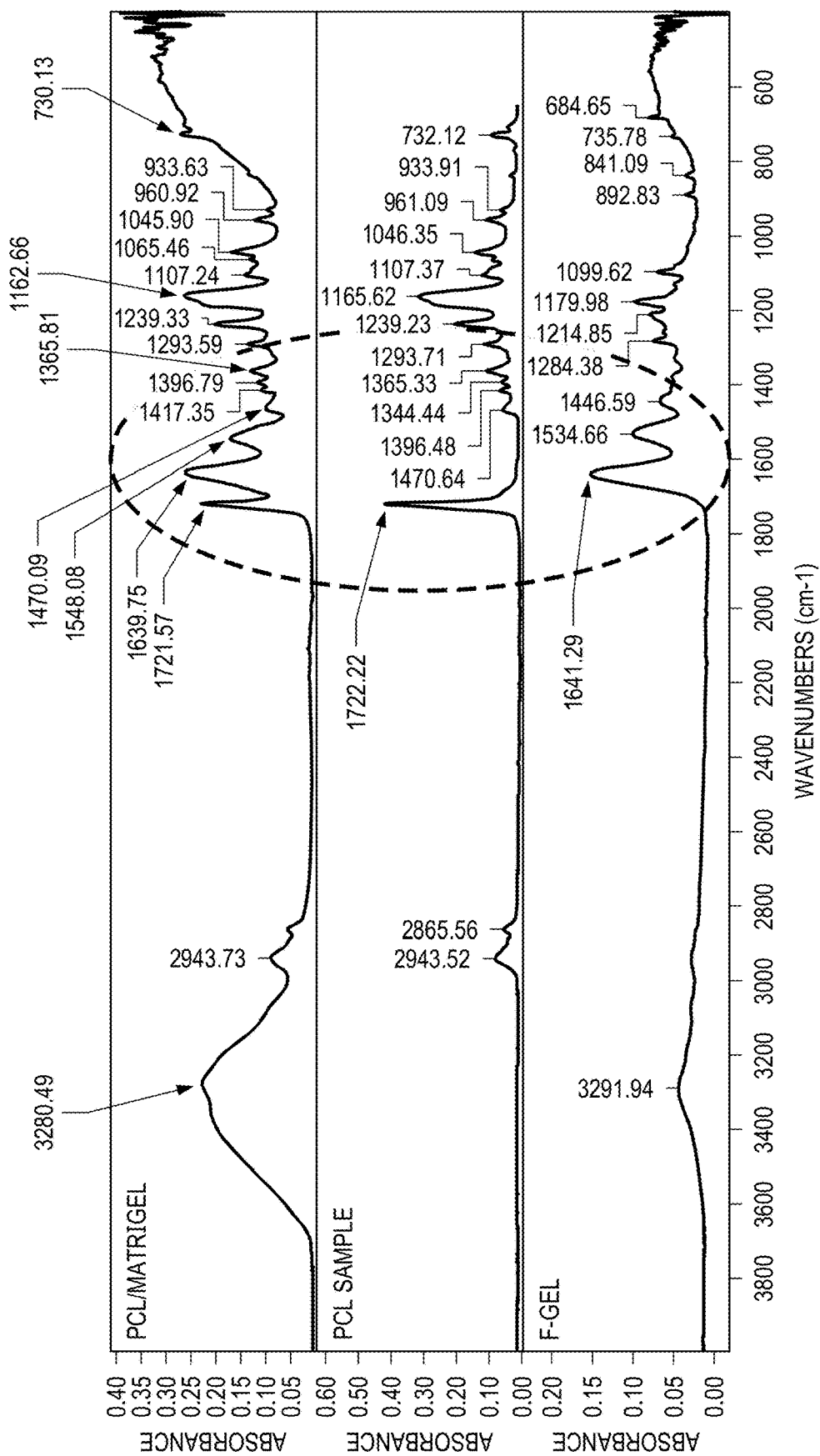

In order to determine the chemical modifications due to addition of PCL to f-gelatin during electrospinning, ATR-FTIR analysis was performed initially to confirm their blending. The pure f-gelatin fibers with and without RF was also analyzed in this experiment. FIGS. 2A-2B show the ATR-FTIR spectra of all electrospun scaffolds. No apparent peaks of the solvent were observed, which proves that there was a complete evaporation of solvent during the electrospinning process. All peaks corresponding to both PCL and f-gelatin, namely the carbonyl, amide I and amide II peaks were observed. Few peaks of PCL and f-gelatin, between 1160-1200 cm$^{-1}$ were found to be overlapping. The presence of f-gelatin in the sample was confirmed from four different regions in the spectra and the two regions that included the 1,656-1,644 cm$^{-1}$ (Amide I) and 1,560-1,335 cm$^{-1}$ (Amide II), respectively. The electrospun spectra showed Amides I and II bands of increasing intensity in case of f-gelatin alone system while the peaks were significantly lower in intensity in the blended systems. The absence of peaks in amide III region (1240-670 cm$^{-1}$) is associated with loss of triple-helix state during denaturation of collagen to gelatin. The carbonyl C═O double bond-stretching mode, with contributions from in-phase bending of the N—H bond and stretching of the C—N bond, occurs in frequency range 1,660-1,620 cm$^{-1}$ region, which is often referred to as Amide I band. The frequency range 1,660-1,650 cm$^{-1}$ was known as α-helical and 1,640-1,620 cm$^{-1}$ as β-sheets structures. The frequency range of 1,550-1,520 cm$^{-1}$ is due to Amide II with a-helical structure between 1,550 and 1,540 cm$^{-1}$ and β-sheets at 1,525-1,520 cm$^{-1}$. The Amide II vibration is caused by deformation of the N—H bonds. The characteristic absorption band at 1,730 cm$^{-1}$ is mainly due to ester carbonyl group, and that at 1,283 cm$^{-1}$ corresponds to the —CH group of PCL. The most eminent peaks are listed in Table 2.

TABLE 2

Prominent peaks of f-gelatin based electrospun fibers

| Wavelength(cm$^{-1}$) | Designation |
|---|---|
| 1700-1750 | C═O stretching |
| 1226-1280 | O—C—O stretching |
| 1636-1640 | C—O stretching of amide I in gelatin |
| 1542-1548 | N—H and C—H stretching in amide II |

The degree of interaction between the blended electrospun systems polymers could not be discerned as all peaks corresponding to both PCL and f-gelatin were observed. Since no interactive peaks were observed and since the interactive peaks may overlap with individual band vibrations of PCL and f-gelatin, thermal analysis was performed to further analyze the interaction/non-interaction of the polymers in the electrospun scaffolds. Moreover, photo-crosslinking of f-gelatin showed no new peaks.

Figure 3A:
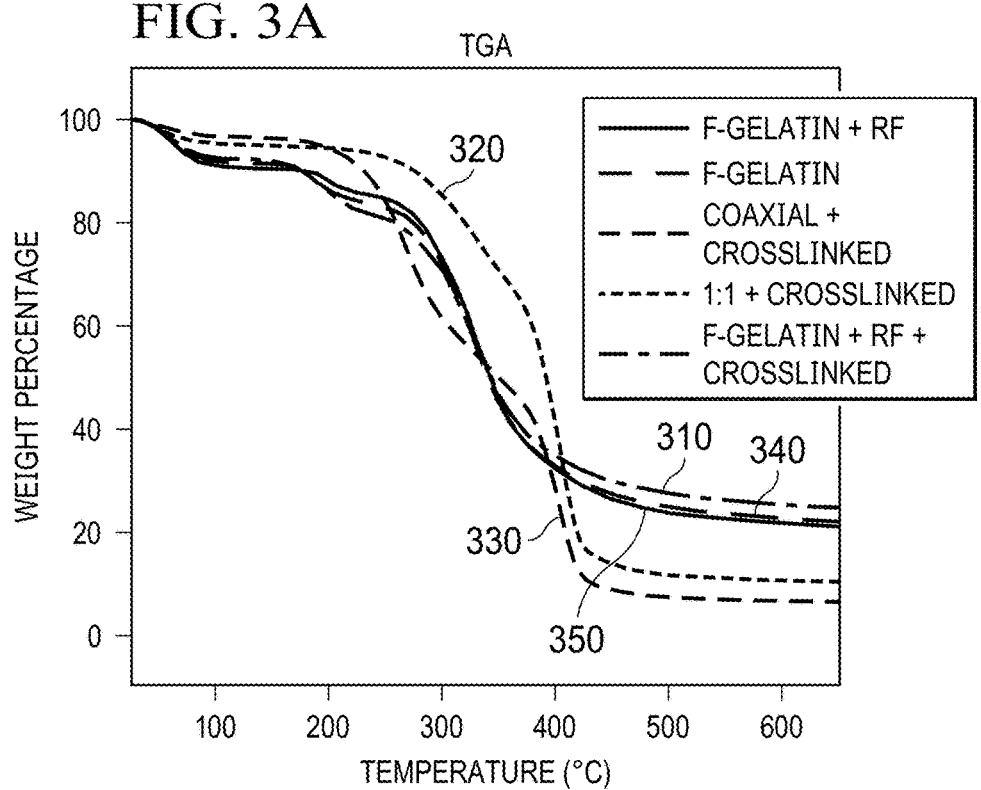
FIGS. 3A-3B illustrate: A TGA of all electrospun scaffolds; and B DSC of all electrospun scaffolds.

TGA thermograms of blended electrospun scaffolds that were crosslinked are shown in FIG. 3A. The black thermogram 310 is for f-gelatin with riboflavin, crosslinked. The red trace 320 is for 1:1 f-gelatin and PCL, crosslinked. The blue trace 330 is for coaxial f-gelatin over PCL, crosslinked. The pink trace 340 is for f-gelatin. The green trace 350 is for f-gelatin with riboflavin.

A three-stage weight loss of samples was observed for all electrospun samples. The first stage corresponds to the loss of moisture from these samples, while the second and third correspond to the thermal decomposition of gelatin and PCL. The loss of moisture in gelatin occurred over a temperature range of 21-90° C. and marked the first stage of weight loss. The first weight loss was correspondingly higher for the f-gelatin alone electrospun scaffolds and considerably lower in the blended electrospun scaffolds which was apparent from the $T_{-5\%}$ values as listed in Table 3. $T_{-5\%}$ values represent the initial weight loss of the material used for analysis. The higher $T_{-5\%}$ value represents a higher thermal stability of the material.

TABLE 3

Thermal analysis of f-gelatin based electrospun fibers

|  | F-gelatin | F-gelatin and PCL(1:1) | Coaxial f-gelatin > PCL |
|---|---|---|---|
| Tmax1(° C.) | — | 276.5 | 223.03 |
| Tmax2(° C.) | 278.33 | 376.38 | 380.56 |
| T-5%(° C.) | 71.67 | 140.28 | 187.07 |
| Denaturation temperature(° C.) $T_D$ | 42.52 | 41.12 | 40.6 |
| Melting Temperature(° C.) $T_m$ | — | 61.2 | 56.08 |

$T_{max}$ values are temperatures at which maximum mass rate change occurs and two separate $T_{max}$ values corresponding to the degradation of f-gelatin and PCL were observed, respectively. With different blending of PCL with f-gelatin, the $T_{max2}$ values were found to differ correspondingly. The $T_{max2}$ values correspond to β-sheet thermal decomposition in gelatin, which further proves that the addition of gelatin resulted in relatively easy crystallization and increased β-sheet content. The $T_{max1}$ values correspond to the degradation initiated from chain scission of the ester linkage in PCL. Since the degradation steps correspond to the individual polymers, no interaction between the polymers in the electrospun scaffolds was observed through TGA.

Figure 3B:
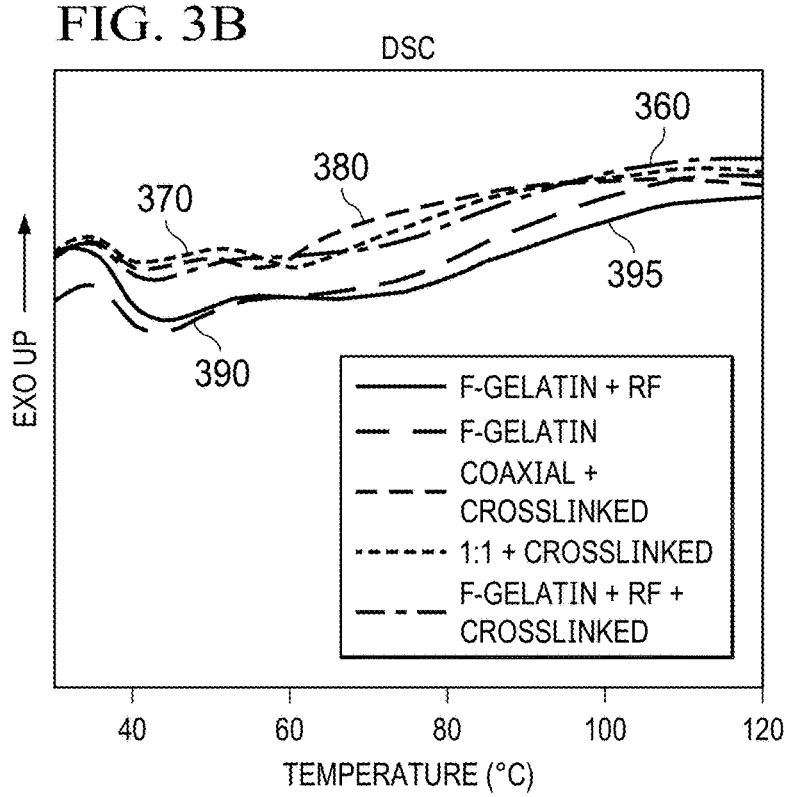

FIG. 3B represents the DSC of the electrospun scaffolds. The black DSC 360 is for f-gelatin with riboflavin, crosslinked. The red DSC 370 is for 1:1 f-gelatin and PCL, crosslinked. The blue DSC 380 is for coaxial f-gelatin over PCL, crosslinked. The pink DSC 390 is for f-gelatin. The green trace 395 is for f-gelatin with riboflavin.

Despite gelatin being a denatured product form of collagen, which involves rupture of the triple-helix structure by breaking of hydrogen bonds and a rearrangement of the triple-helix into a random configuration, renaturation is possible under certain conditions. Therefore, the characteristic endothermic peaks of gelatin have often been termed as denaturation temperature ($T_D$). Miscible polymers have a single-phase blend due to which a single glass transition, a single crystallization, and a single melting transition is observed. On the contrary, an immiscible blend typically shows two inflections or endotherms due to the glass transition and/or melting endotherms, although they are expected to deviate from those of the pure components. Hence, PCL and f-gelatin are thermodynamically immiscible polymers. Furthermore, f-gelatin and PCL (1:1) electrospun scaffolds exhibited significantly higher $T_m$ (melting temperature) when compared to the coaxial f-gelatin>PCL electrospun system. An increased pressure and temperature when heat is transferred from the f-gelatin sheath to the PCL core led to the significant decrease in $T_m$ of PCL in coaxial f-gelatin>PCL scaffolds. Since no third interactive peak was observed from DSC it conclusively proved the non-interaction of the polymers after electrospinning and crosslinking. Thermal analysis also conclusively proves that the coalescence of fibers observed in the coaxial f-gelatin>PCL electrospun scaffolds were physical in nature alone with no chemical interactions.

Mechanical Stability of Electrospun Scaffolds

Figure 4:
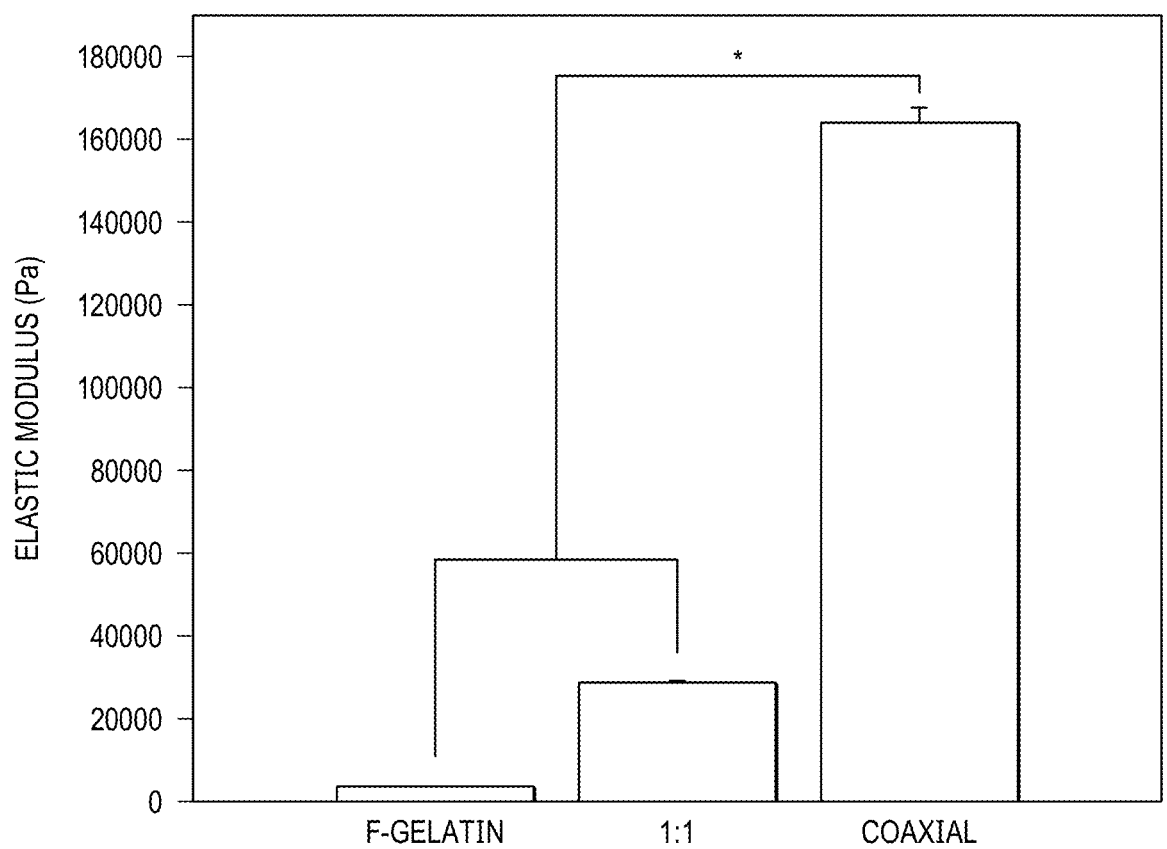
FIG. 4 shows elastic modulus of different electrospun scaffolds obtained through rheological analysis. F-gelatin is labeled as F-GEL; f-gelatin and PCL (1:1) is labeled as 1:1 and coaxial f-gelatin>PCL electrospun scaffolds is labeled as COAX.

Rheometric analysis was performed on the crosslinked electrospun scaffolds after 12 hours of pre-swelling in 1×PBS (pH 7.4) and is presented in FIG. 4. At 1% constant strain, the average elastic modulus of f-gelatin electrospun scaffolds was 3.46±0.05 kPa and was 28.49±0.26 kPa for the f-gelatin and PCL (1:1) scaffolds. The average elastic modulus of the coaxial f-gelatin>PCL scaffolds was 164±3.85 kPa. The addition of PCL to the blended scaffolds was found to significantly improve the elastic modulus of the scaffolds (p=0.02). In case of f-gelatin and PCL (1:1) electrospun scaffolds, the topical addition of PCL to f-gelatin polymer solution merely contributed to the enhancement of the elastic modulus of the resultant scaffold. However, for the coaxial f-gelatin>PCL scaffolds, a significantly higher elastic modulus was recorded. Hence, the coaxial f-gelatin>PCL electrospinning process significantly improved the mechanical stability of the fibrous scaffolds. Moreover, the physical coalescence of fibers at the junctions in coaxial f-gelatin>PCL electrospun scaffolds also led to their enhanced elastic modulus. The elastic modulus of the blended scaffolds fell within the range of the native ECM present in the human myocardium and can be potentially utilized as platforms or scaffolds for cardiac tissue engineering.

In Vitro Degradation Studies of Electrospun Scaffolds

Figure 5A:
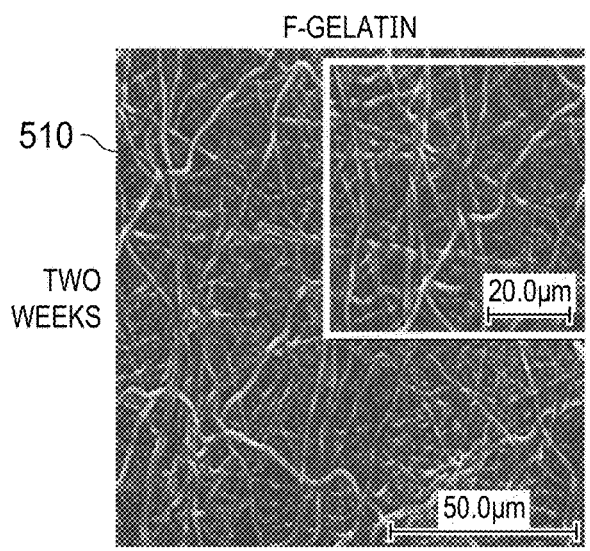
FIGS. 5A-5H are: A-C SEM images of in vitro degradation of f-gelatin; f-gelatin and PCL (1:1) and coaxial f-gelatin>PCL electrospun scaffolds after 2 weeks (Scale bar 50 µm/20 µm (inset)); D-F SEM images of in vitro degradation of f-gelatin; f-gelatin and PCL (1:1) and coaxial f-gelatin>PCL electrospun scaffolds after 3 weeks (Scale bar 50 µm/20 µm(inset)); and G-H schematic representation of degradation mechanism in blended electrospun scaffolds.
Figure 5B:
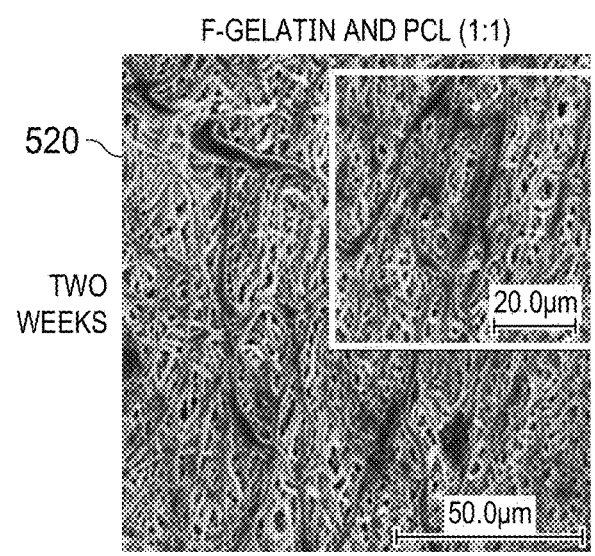
Figure 5C:
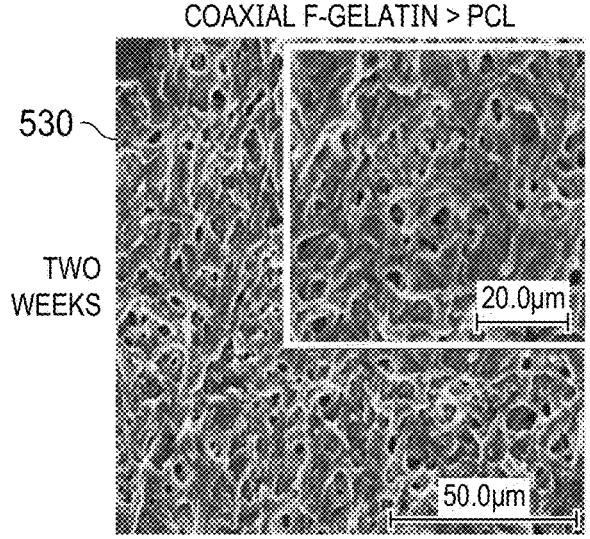
Figure 5D:
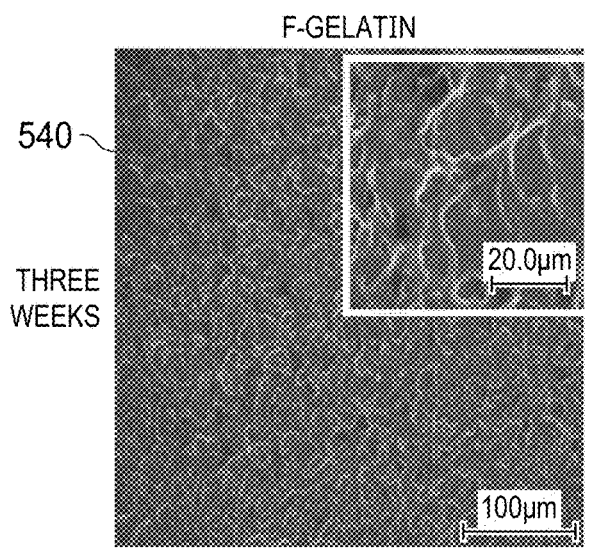
Figure 5E:
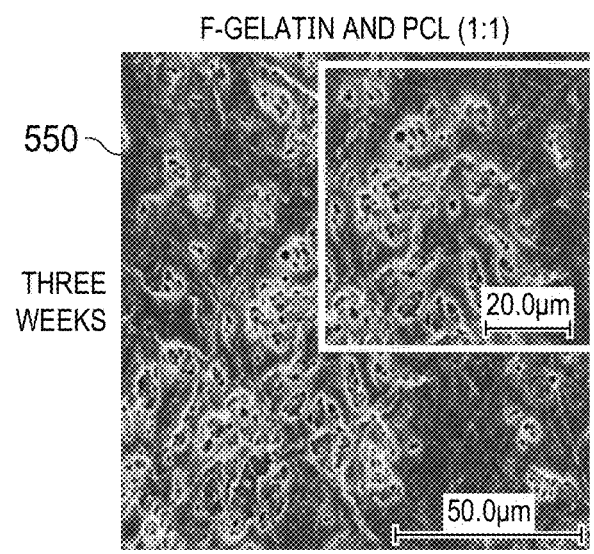
Figure 5F:
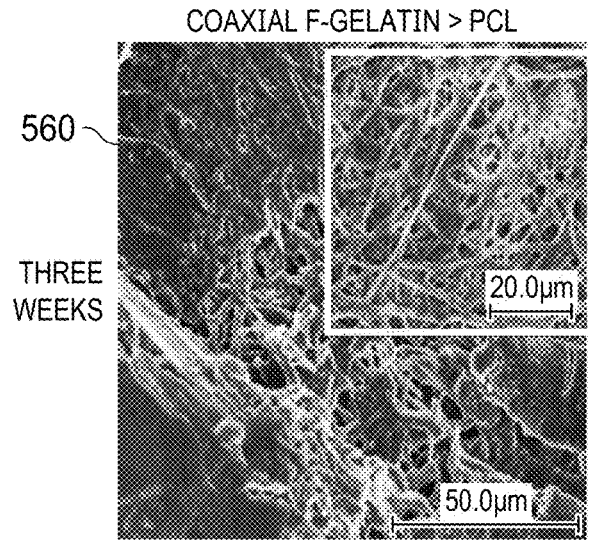

FIGS. 5A-5F show the SEM images of in vitro degradation of blended crosslinked fibers of f-gelatin, f-gelatin and PCL (1:1) and coaxial f-gelatin>PCL systems after 2 (FIGS. 5A-5C) and 3 weeks (FIGS. 5D-5F), respectively. FIG. 5A shows f-gelatin 510 at 2 weeks. FIG. 5B shows 1:1 blend of f-gelatin and PCL 520 at 2 weeks. FIG. 5C shows coaxial f-gelatin over PCL 530 at two weeks. FIG. 5D shows f-gelatin 540 at three weeks. FIG. 5E shows 1:1 blend of f-gelatin and PCL 550 at three weeks. FIG. 5F shows coaxial f-gelatin over PCL 560 at three weeks.

Figure 5G:
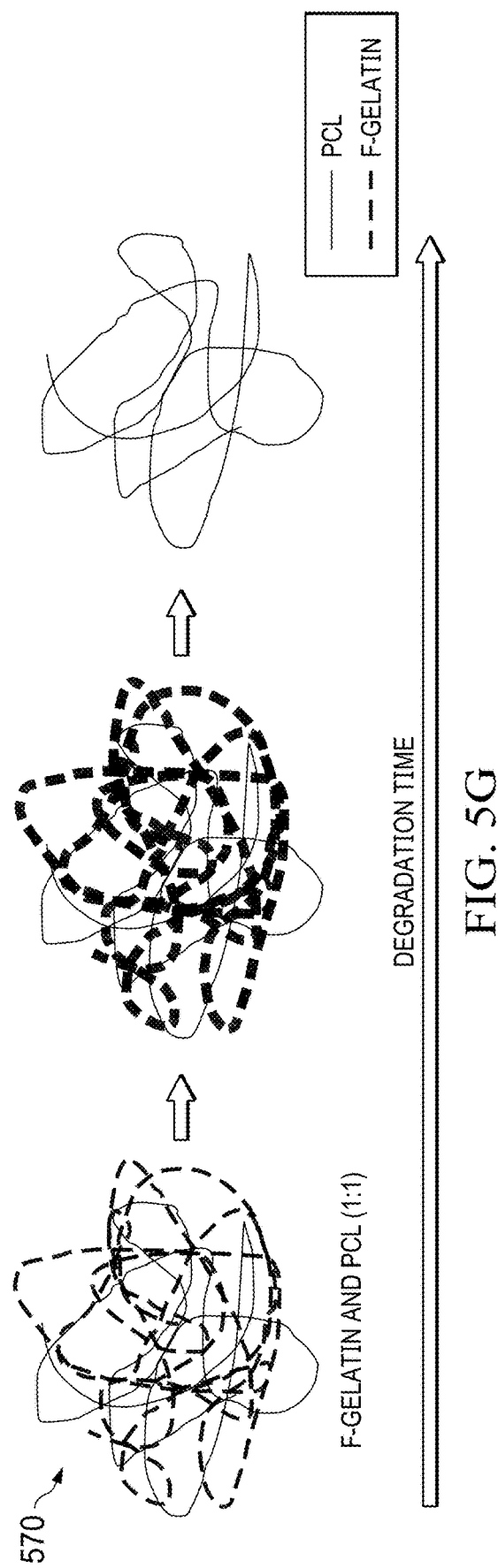
Figure 5H:
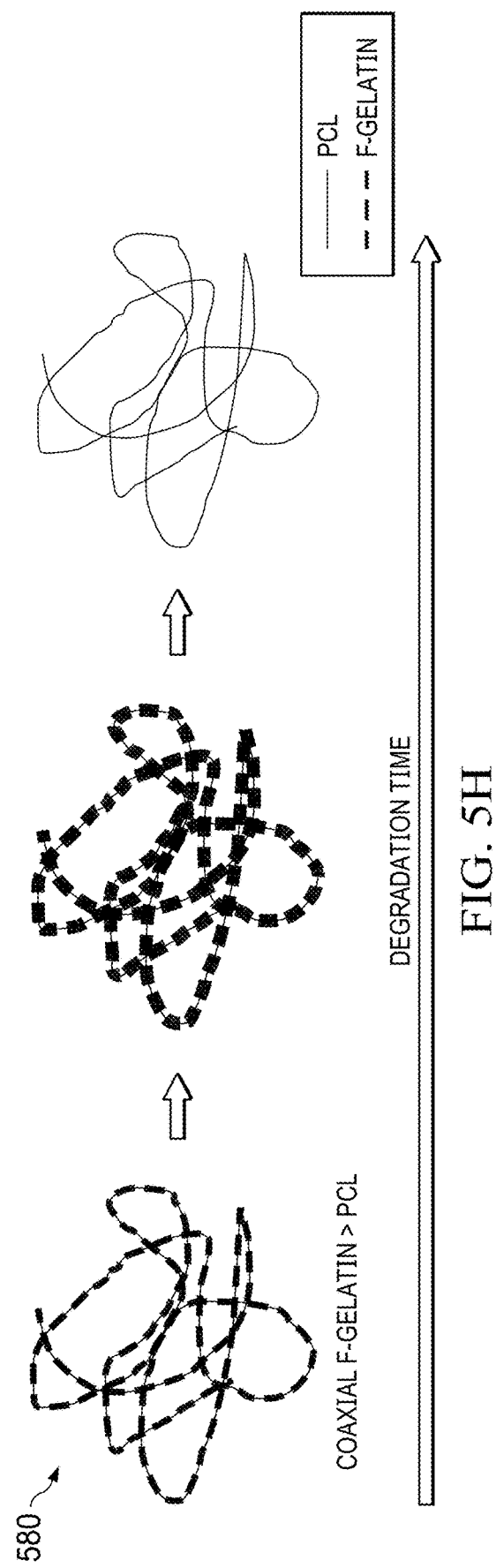

FIG. 5G shows degradation as a function of time for 1:1 f-gelatin and PCL blend 570. FIG. 5H shows degradation as a function of time for coaxial f-gelatin over PCL 580.

Swelling of the fibers were detected in all electrospun scaffolds. The swelling pattern was significantly pronounced in pure f-gelatin electrospun scaffolds and least pronounced in the blended f-gelatin and PCL (1:1) system. The degree of swelling was directly proportional to the composition of f-gelatin present in the sample (FIGS. 5G-5H). Correspondingly, changes in morphology of the fibers were increasingly pronounced with the presence and composition of f-gelatin. PCL being a hydrophobic polymer was found to undergo surface erosion degradation, while gelatin present in the fibers corresponded to bulk degradation of the fibers. The porosity and pore structure of the electrospun scaffolds are significantly affected by the swelling of f-gelatin after 2 weeks. The higher degree of swelling in f-gelatin electrospun scaffolds and coaxial f-gelatin>PCL scaffolds led to the complete occlusion of pores within 2 weeks. After 3 weeks, the high degree of swelling in f-gelatin electrospun scaffolds led to the disruption of its fibrous nature while in coaxial f-gelatin>PCL scaffolds the partial degradation of the f-gelatin sheath exposed the internal PCL fibers in the scaffold. The blended f-gelatin and PCL (1:1) electrospun scaffolds clearly showed the chemical non-interaction of gelatin and PCL fibers during the study. The swelling of f-gelatin is clearly visible after 2 weeks and was found to be more pronounced after 3 weeks. The occlusion of pores was minimal in the blended f-gelatin and PCL (1:1) electrospun scaffolds and was highest in f-gelatin electrospun scaffolds. The hydrophilicity of the gelatin structure leads to bulk degradation of the shell structure. The obtained results conclusively indicate that the increase in f-gelatin composition increased the biodegradability of the scaffold.

Biocompatibility of the Electrospun Scaffolds

FIGS. 6A-6E represent the adhesion of AC16 cardiomyocytes on all the electrospun scaffolds. The three sets of electrospun scaffold groups shown in FIGS. 6A-6C were found to support the adhesion of AC16 cardiomyocytes after only 24 hours of culture.

Figure 6A:
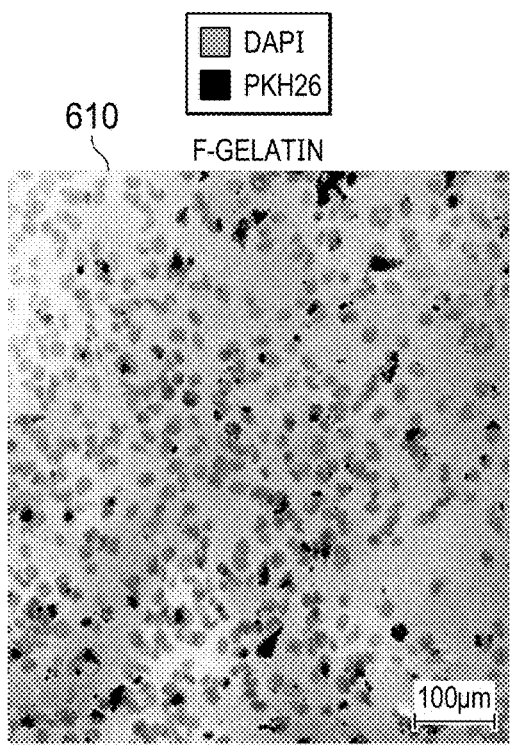
FIGS. 6A-6E are confocal microscopy images of DAPI (blue) and PKH26 (red) stained AC16 cardiomyocytes on f-gelatin; f-gelatin and PCL (1:1) and coaxial f-gelatin>PCL electrospun scaffolds after 24 hours (Scale bar 100 µm).
Figure 6B:
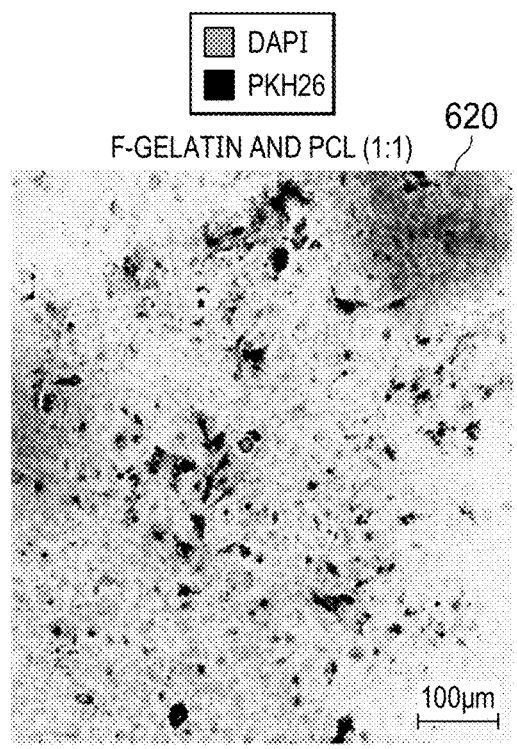
Figure 6C:
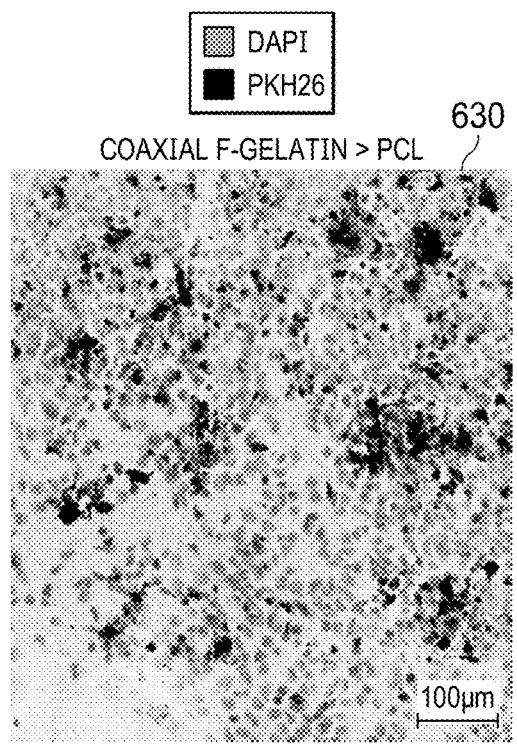

FIG. 6A shows f-gelatin 610. FIG. 6B shows 1:1 f-gelatin and PCL 620. FIG. 6C shows coaxial f-gelatin over PCL 630. It can be appreciated that there is less adhesion with f-gelatin 610.

Figure 6D:
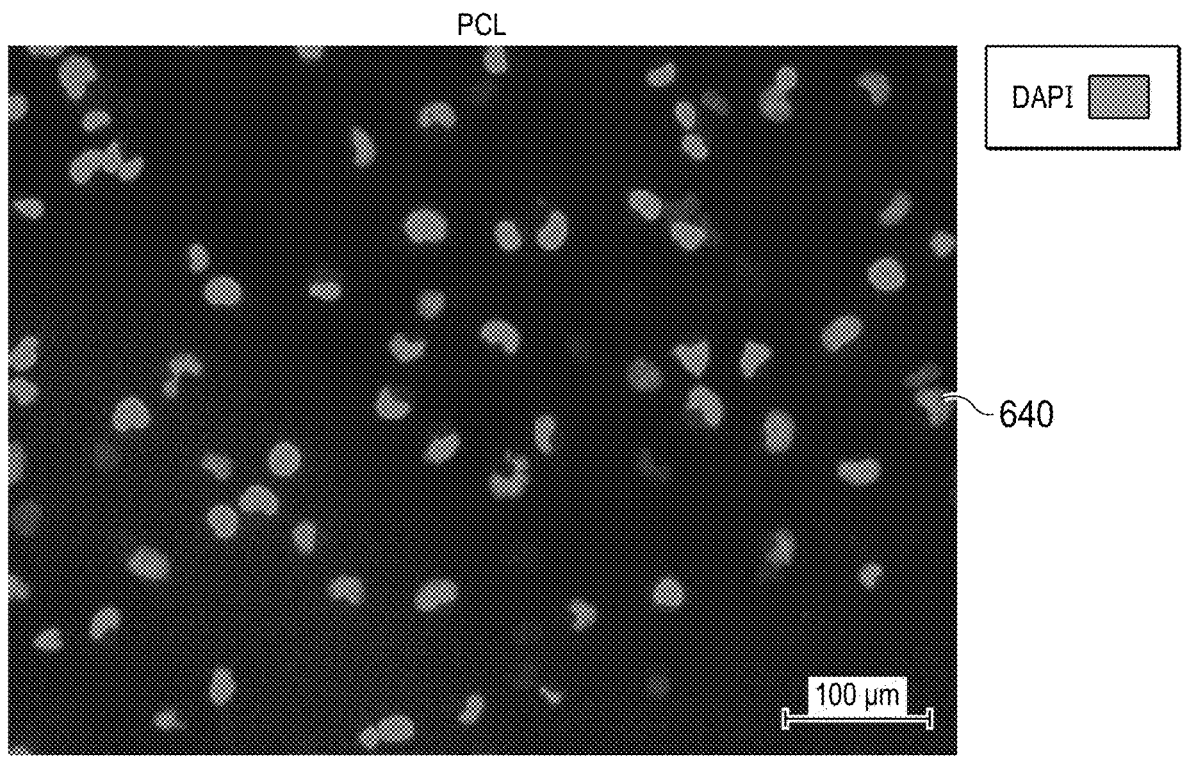
Figure 6E:
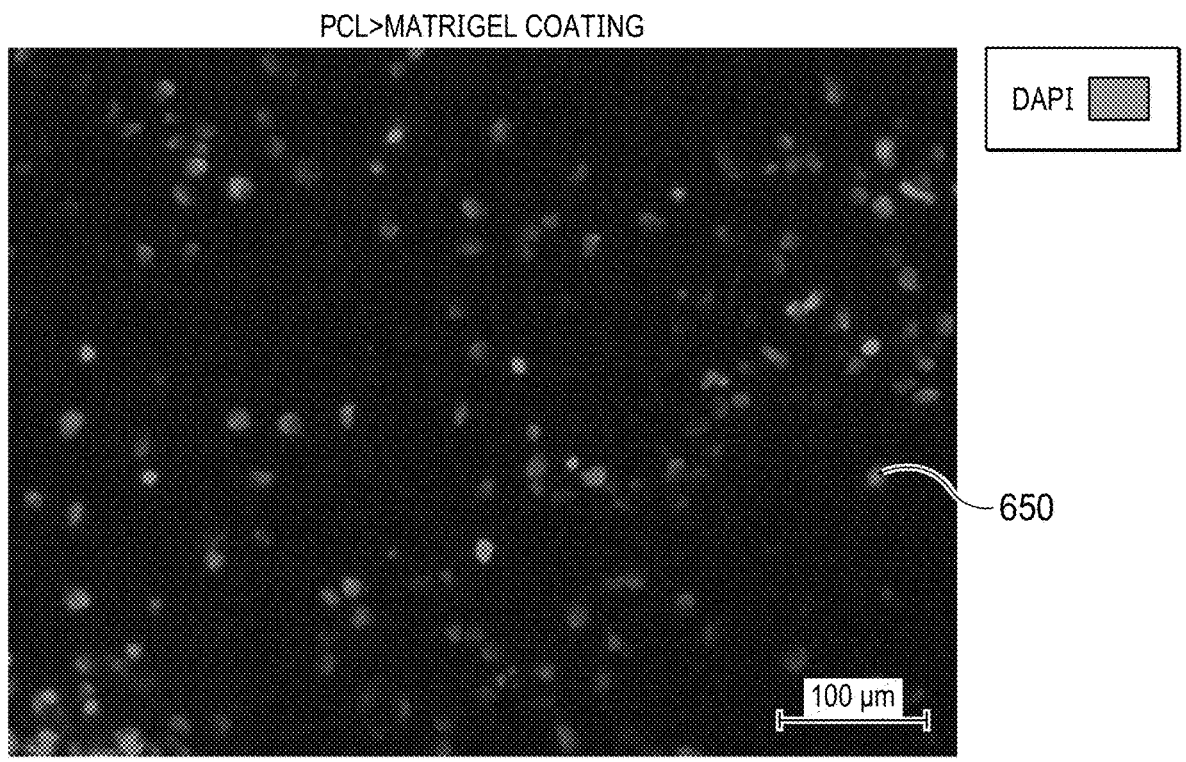

The two sets of electrospun scaffold groups shown in FIGS. 6D-6E were found to support the adhesion of AC16 cardiomyocytes after only 24 hours of culture and continuous viability. FIG. 6D shows DAPI results 640 with PCL. FIG. 6E shows DAPI results 650 with matrigel coating over PCL. Images were obtained after an incubation period of 7 days, with one media change at day 3.

The percentage of adhered cells studied through PK26 cell-labelling using Image J software showed significantly improved adhesion of cells on blended electrospun f-gelatin and PCL (1:1) (~64%) and coaxial f-gelatin>PCL scaffolds (~68%) than f-gelatin electrospun scaffolds (~39%). The significant difference in elastic modulus was sensed by the cells and led to a higher adhesion of cells on blended scaffolds with higher elastic modulus. The exposure of RGD cell binding sequence in f-gelatin enables the adhesion of the cardiomyocytes to the scaffolds. Moreover, the high surface to volume ratio created by the surface roughness of the electrospun fibrous scaffolds also provide an optimal substrate for the cells to adhere within 24 hours. Without being bound by theory, the improved adhesion is an unexpected, commercially advantageous result provided by embodiments of this disclosure.

Figure 7A:
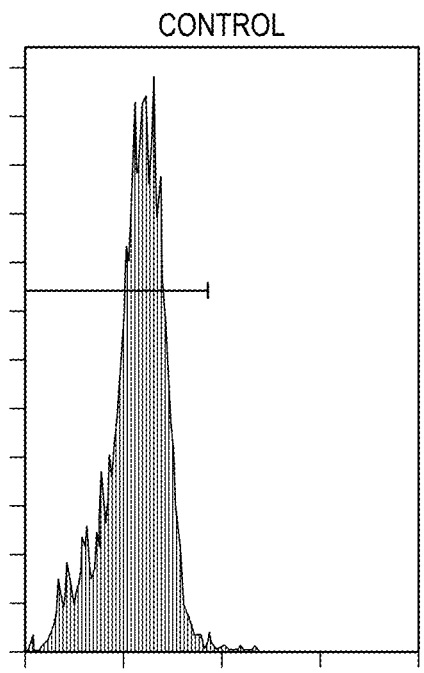
FIGS. 7A-7H illustrate flow cytometry analysis of: A CTV unstained cardiomyocytes extracted from cell culture plates after 48 h; B CTV stained cardiomyocytes extracted from cell culture plates after 48 h; C, E, G CTV stained cardiomyocytes extracted from f-gelatin; f-gelatin and PCL (1:1) and coaxial f-gelatin>PCL electrospun scaffolds after 24 h; and D, F, H CTV stained cardiomyocytes extracted from f-gelatin; f-gelatin and PCL (1:1) and coaxial f-gelatin>PCL electrospun scaffolds after 7 days.
Figure 7B:
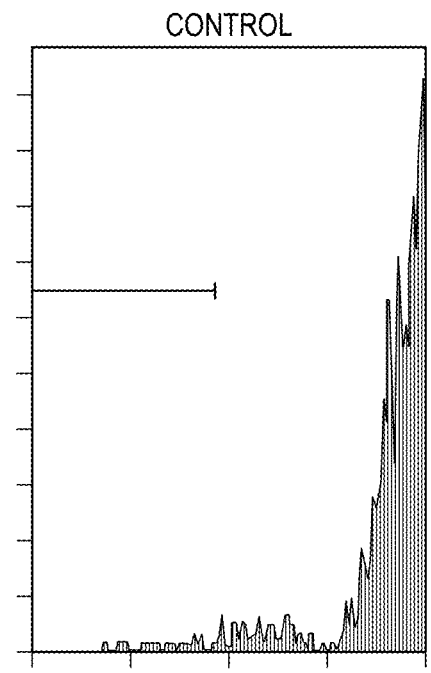
Figure 7C:
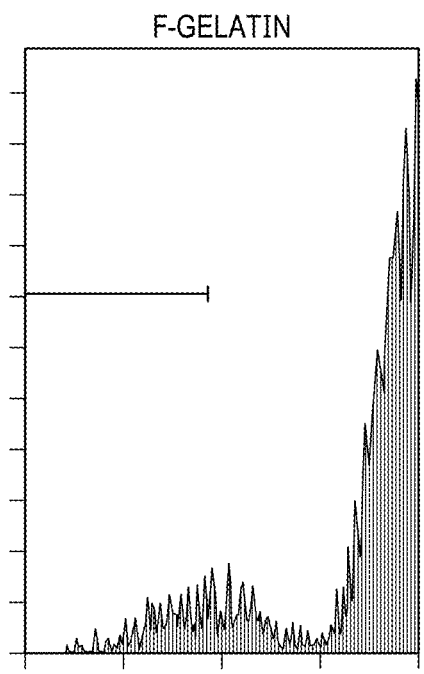
Figure 7D:
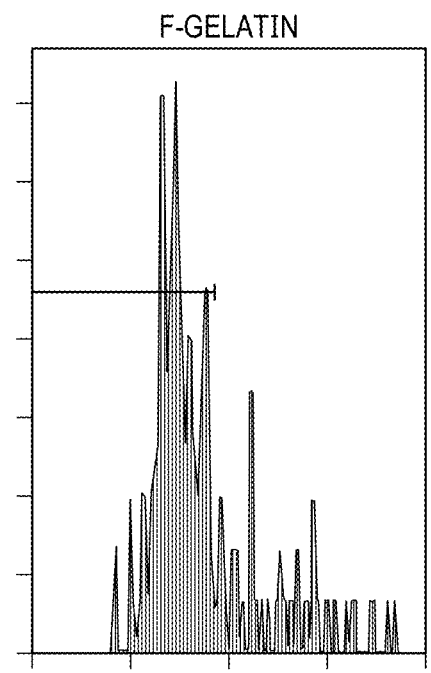
Figure 7E:
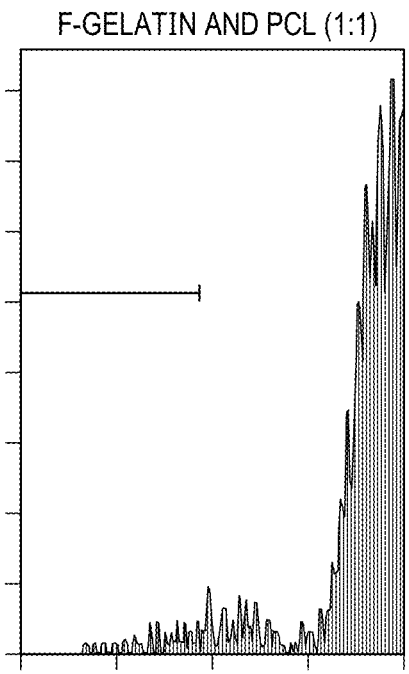
Figure 7F:
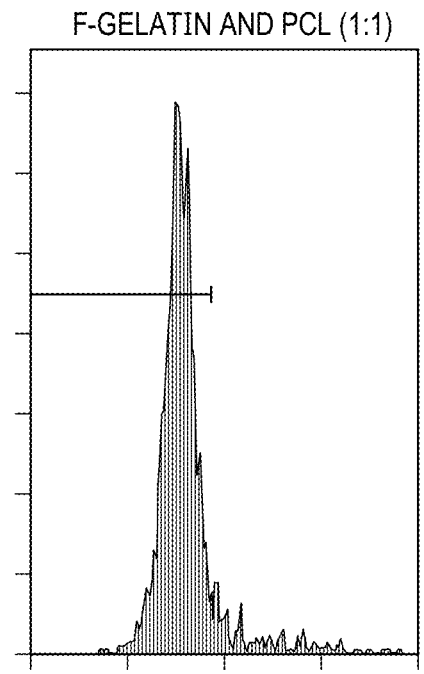
Figure 7G:
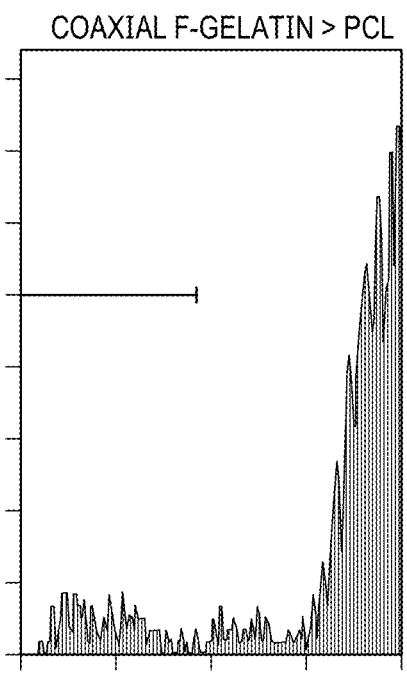
Figure 7H:
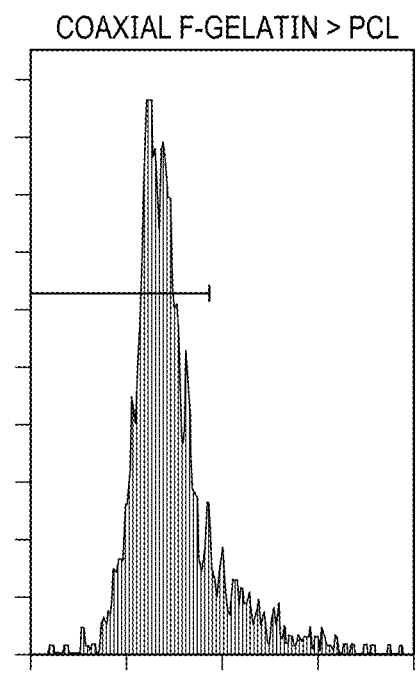

FIGS. 7A-7H present FACS (flow cytometry analysis) of cardiomyocytes extracted from all the electrospun scaffolds. The cardiomyocytes were stained using CellTrace™ Violet (CTV) dye to track cell growth and proliferation using the concept of dye dilution after 1 and 7 days of culture. Since cell doubling time for AC16 cardiomyocytes is ~25 hours, cell proliferation caused a reduction in intensity of the dye over successive generations thereby permitting the analysis of several generations of proliferating cells within 7 days. For FIGS. 7A-7H, the vertical axis can be labeled counts; and FL10 can be labeled on the horizontal axis at the second marker to the right of the vertical axis. In this experiment, positive controls included cells pre-stained with CTV (FIG. 7A) and cultured for 48 hours after which they were extracted. Negative controls (FIG. 7B) included samples cultured using exact conditions as positive controls, without the addition of the CTV dye. The characteristic peaks from negative controls are observed in the low intensity region in left and peaks for positive stained cells with high intensity is observed in right. FIGS. 7C, 7E and 7G represent the CTV pre-stained cells extracted from f-gelatin, blended f-gelatin and PCL (1:1) and coaxial f-gelatin>PCL electrospun scaffolds on day 1 showed peaks in the positive control region signifying the adhesion of cells on the scaffolds. Since the time period for proliferation was low, most of the cells exhibited higher concentration of the dye. FIGS. 7D, 7F and 7H represents the CTV pre-stained cells extracted from f-gelatin, blended f-gelatin and PCL (1:1) and coaxial f-gelatin>PCL electrospun scaffolds on day 7, respectively. The intensity of the CTV dye significantly decreased and moved to the negative control region at day 7. This significant reduction in intensity of the dye clearly signified the dilution of dye with time indicating proliferation of the pre-stained cardiomyocytes on the electrospun scaffolds.

Figure 8A:
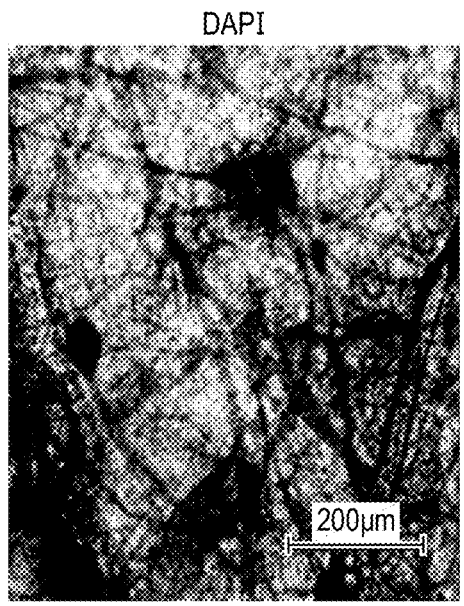
FIGS. 8A-8C are confocal microscopy images of DAPI and PKH26 stained hiPSC derived cardiomyocytes on all electrospun scaffolds after 72 hours (scale bar 200 µm).
Figure 8B:
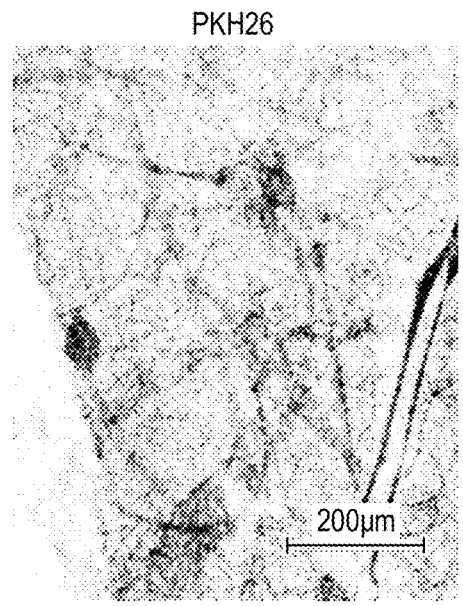
Figure 8C:
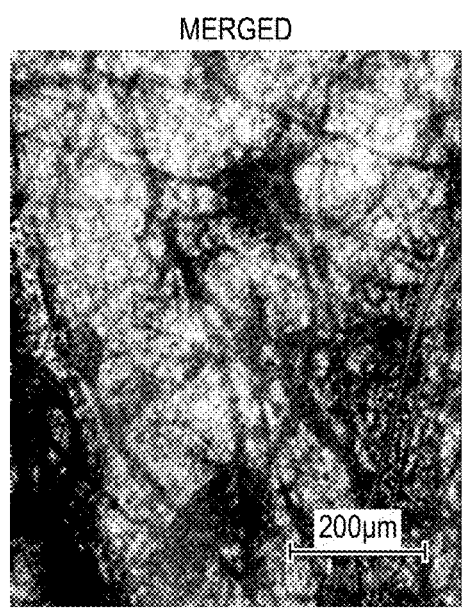

Studying the Coaxial f-Gelatin>PCL Electrospun Scaffolds as Potential Platform for Cardiac Tissue Engineering Since coaxial f-gelatin>PCL electrospun scaffolds exhibited significantly higher elastic modulus when compared to other scaffolds, Cellartis hiPSCs-cardiomyocytes were seeded on them to study their biocompatibility. FIGS. 8A-8C represents the adhesion of cells on the coaxial f-gelatin>PCL electrospun scaffolds after 3 days thereby providing appropriate time for the cells to attach and adapt to the scaffold. FIG. 8A shows a confocal microscope image of DAPI stained hiPSC derived cardiomyocytes after 72 hours. FIG. 8B shows a confocal microscope image of PKH26 stained hiPSC derived cardiomyocytes after 72 hours. FIG. 8C shows a merged confocal microscope image of the separate images of FIGS. 8A-8B. The contractile function of the hiPSC-cardiomyocytes on the electrospun scaffolds was intact and shown in a video available at (https://drive.google.com/file/d/1E1iyqf0ohlz2cTv5tyan2eUi1_X_vUE0/view?usp=sharing).

Figure 10A:
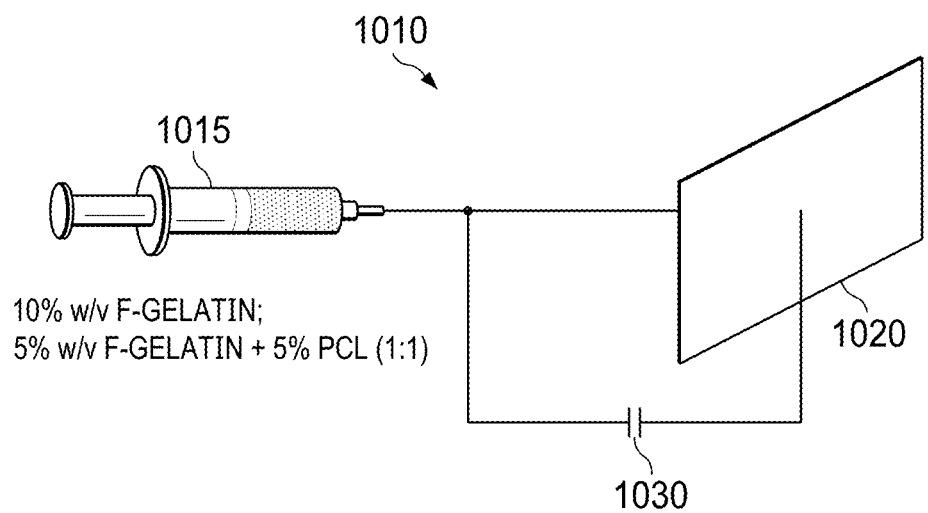
FIGS. 10A-10B are schematic views of: A apparatus for uniaxial nozzle (single nozzle) electrospinning; and B apparatus of coaxial nozzle (multiple nozzle) electrospinning.

FIG. 10A shows a schematic view of a basic apparatus for uniaxial electrospinning 1010. A source of polymer solution in the form of syringe pump 1015 is coupled to collector 1020. Syringe pump 1015 contains a blend of i) 10% f-gelatin and ii) 5% f-gelatin & 5% PCL. A power supply 1030 is coupled to syringe pump 1015 and collector 1020.

Figure 10B:
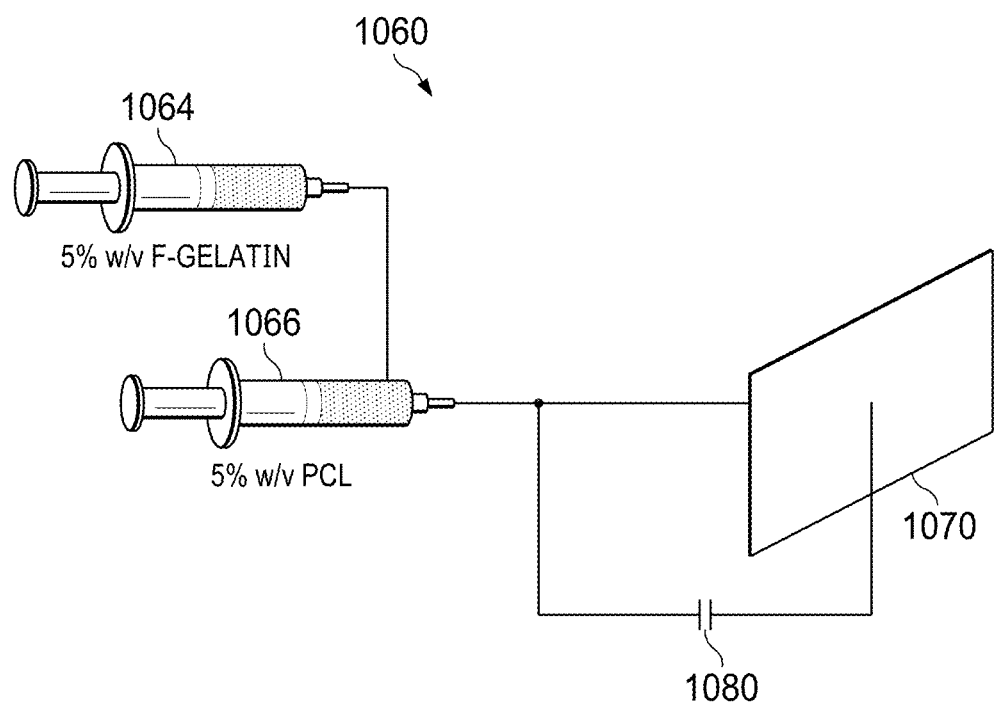

FIG. 10B shows a schematic view of an apparatus for coaxial electrospinning 1060. A source of a first polymer solution in the form of syringe pump 1064 is coupled to a source of a second polymer solution in the form of syringe pump 1066. Syringe pump 1066 is coupled to collector 1070. The first polymer solution and the second polymer solution are pumped in parallel through a coaxial nozzle in syringe pump 1066. In this way, the 2 polymer solutions are pumped from the coaxial nozzle. A power supply 1080 is coupled to syringe pump 1066 and collector 1070.

Electrospinning has witnessed a profound advancement in the field of tissue engineering and regenerative medicine. The versatility of the electrospinning process combined with the emergence of new biopolymers has been major accelerator of this growth. The present study demonstrates the applicability of using an f-gelatin and PCL based electrospun fibrous scaffolds geared toward cardiac tissue engineering applications. The f-gelatin comprised porcine gelatin, modified by the incorporation of a furfural group. Earlier studies by our group on this f-gelatin led to the development of a scaffold that can be rapidly crosslinked in the presence of visible light to maintain structural fidelity. However, the structural integrity and stiffness of the printed crosslinked structure improved only when blended with hyaluronic acid. Our long-term goal is to biofabricate multilayered, multicellular models which can be used for mimicking in vivo cardiac tissue. Since, the topographies of scaffolds has been shown to dictate cellular attachment, migration, proliferation, and differentiation, which are critical in engineering complex functional tissues with improved biocompatibility and functional performance electrospinning of f-gelatin with PCL was chosen as the method to develop the needed platforms for cardiac tissue modeling.

As a first step, we developed a novel visible light crosslinked electrospun scaffolds based on f-gelatin and PCL, which would aid providing ideal platforms for cardiac modeling applications. In comparison with f-gelatin 3D bioprinted gels reported by our group in prior studies, the f-gelatin electrospun scaffolds possessed improved mechanical properties as well as optimal swelling behavior. Electrospinning of polymer solutions requires the optimization of various parameters i.e. concentration, viscosity, molecular weight, degree of entanglement, electrical conductivity, and surface tension. The hydrophobic synthetic polymer PCL has been electrospun using solvents such as dichloromethane and chloroform. Due to higher conductivity and solubility factors, 1,1,1,3,3,3 HFP has been widely used to electrospun natural polymers. Moreover, HFP also reduces surface tension of the polymer solution thereby enabling blending of natural polymers with synthetic polymers. Hence HFP was chosen as the optimal solvent for electrospinning f-gelatin and blended f-gelatin and PCL fibers. The increase in diameter of coaxial f-gelatin>PCL fibers over f-gelatin and f-gelatin and PCL (1:1) blended fibers has been attributed to the presence of PCL core solution that caused a difference in charge relaxation time and viscosity of the coaxial f-gelatin>PCL spinning solution. The increase in fiber diameter corresponds to a decrease in surface area of the electrospun fibers which might influence a decrease in adhesion of cells on the coaxial f-gelatin>PCL scaffolds. Thermal properties of the electrospun fibers were used to assess the miscibility and interaction of the polymer/s after electrospinning. However, no interactive peaks were exhibited by the scaffolds concluding that no interaction occurred between the polymers after electrospinning and crosslinking.

In comparison with other types of hybrid blended gelatin scaffolds, these scaffolds produced via a simple visible light crosslinking mechanism can maintain non-interaction between polymers which will aid in maintain the structural and functional properties of growth factors or other chemokines for releasing into the culture or in vivo, as desired as visible light crosslinking does not seem to alter the chemical functionality of the polymers. However, in vitro degradation studies performed on all the systems exhibited stark differences in the structural stability of the scaffolds over a 3-week period. Blended electrospun scaffolds were more structurally stable than f-gelatin electrospun scaffolds. The addition of hydrophobic PCL significantly improved the structural stability of the scaffolds. Moreover, the swelling and degradation of gelatin in the blended scaffolds increased the pore diameter of the scaffolds which thereby enabled the penetration of cells through the scaffolds. All electrospun scaffolds exhibited excellent biocompatibility by supporting the adhesion and proliferation of human AC16 cardiomyocytes over a period of 7 days. Cardiomyocytes prefer a hydrophobic surface for adhesion and proliferation. Moreover, an increase in water uptake usually causes a decrease in cell adhesion. However, the cell binding sequences in f-gelatin balanced the swelling and the hydrophilic surface properties of f-gelatin.

We aim to fabricate cardiac wall tissue in vitro utilizing electrospinning which can then be exploited in vitro for the drug studies or probing into underlying mechanisms involved in cardiac development and disease. The cross-linked electrospun scaffolds had elastic moduli ranging from 3 to 160 kPa which were stable when exposed to long term culture implying they can be extremely effective for in vivo studies as well. The human myocardium ranges in stiffness from 20 kPa (end of diastole) to 500 kPa (end of systole). Hence, coaxial f-gelatin>PCL electrospun scaffold system which possessed the highest elastic modulus (>150 kPa) among the three electrospun systems was chosen as the potentially suitable candidate for cardiac platforms which could withstand the contractile forces of the native myocardium. Moreover in this study, we cultured human induced pluripotent stem cell derived cardiomyocytes on the chosen coaxial f-gelatin>PCL electrospun scaffolds. The viability and contractile function of the hiPSC-cardiomyocytes were not affected by the coaxial f-gelatin>PCL electrospun platform thereby confirming its potential as an ideal platform for cardiac tissue engineering applications.

Coaxial f-gelatin>PCL electrospun scaffolds of PCL (core) and f-gelatin (sheath) exhibited improved structural and mechanical stability in comparison with electrospun scaffolds developed from f-gelatin alone and conventionally blended f-gelatin and PCL (1:1) scaffolds. The blending of f-gelatin with PCL significantly improved its mechanical and chemical structural stability. The non-interaction of PCL with f-gelatin in the blended scaffolds will aid in addition of drug molecules like growth factors and chemokines without any change in its structural and functional ability. Future studies will be aimed at testing the in vitro efficacy of the coaxial f-gelatin>PCL electrospun scaffolds with appropriately bound drug molecules and developing a robust cardiac organoid platform for drug screening applications.

In conclusion, we showed the applicability of f-gelatin as a novel, biocompatible electrospun scaffolds or platforms with cardiac tissue ECM like mechanical properties. Although both synthetic and natural materials have been proposed to generate suitable tissue engineering grafts, the ideal material or scaffold for repair and regeneration of cardiac tissue is not yet proposed[28]. In the future, we will attempt to develop hierarchically structured scaffolds with piezoelectric or electro-conductive properties to mimic the native myocardium. This will enable us to generate a functional cardiac patch that can be used for drug cytotoxicity screening or exploring triggers for heart diseases in vitro.

The term biocompatible is intended to mean suitable for use with human or animals without undue adverse side effects, namely toxicity, irritation, or allergic response. The term biodegradable is intended to mean degradable by organisms into simpler stable compounds. The terms nanofiber(s) and nanofibrous are intended to mean fibers having an average diameter of from approximately 1 nm to approximately 1 um, preferably from approximately 310 nm to approximately 870 nm.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component can be configured to perform the action or operation described. For example, the component can have a configuration or design for a structure that provides the component an ability to perform the action or operation that is described in the illustrative examples as being performed by the component. Further, To the extent that terms "includes", "including", "has", "contains", and variants thereof are used herein, such terms are intended to be inclusive in a manner similar to the term "comprises" as an open transition word without precluding any additional or other elements.

Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical applications, and to enable others of ordinary skill in the art to understand the disclosure for various embodiments with various modifications as are suited to the particular use contemplated.

What is claimed is:

1. A composition of matter, comprising:
a furfuryl amine-conjugated gelatin;
a solvent; and
a biocompatible biodegradable crosslinking photo initiator.

2. The composition of matter of claim 1, wherein the biocompatible biodegradable crosslinking photo initiator comprises a biocompatible biodegradable visible light crosslinking photo initiator.

3. The composition of matter of claim 2, wherein the biocompatible biodegradable visible light crosslinking photo initiator comprises riboflavin.

4. The composition of matter of claim 1, further comprising polycaprolactone.

5. The composition of matter of claim 4, wherein the furfuryl amine-conjugated gelatin is blended with the polycaprolactone.

6. The composition of matter of claim 5, wherein the furfuryl amine-conjugated gelatin is blended with the polycaprolactone at a ratio of approximately 1:1 by weight.

7. The composition of matter of claim 4, wherein the furfuryl amine-conjugated gelatin is connected to and coats the polycaprolactone to define a coaxial scaffold having polycaprolactone core and furfuryl amine-conjugated gelatin sheath.

8. The composition of matter of claim 1, wherein the solvent comprises 1,1,1,3,3,3 hexafluoroisopropanol.

9. A method of making nanofibrous scaffold biomaterials, comprising:
 providing a polymer solution comprising
  a furfuryl amine-conjugated gelatin;
  a solvent; and
  a biocompatible biodegradable crosslinking photo initiator; and
 electrospinning the polymer solution to form cross linkable electrospun nanofibers.

10. The method of claim 9, wherein electrospinning comprises uniaxial electrospinning.

11. The method of claim 9, wherein electrospinning comprises coaxial electrospinning.

12. The method of claim 9, further comprising exposing at least a portion of the polymer solution to visible light after electrospinning.

13. The method of claim 12, further comprising rinsing at least a portion of the polymer solution after exposing.

14. The method of claim 9, wherein the biocompatible biodegradable crosslinking photo initiator comprises a biocompatible biodegradable visible light crosslinking photo initiator.

15. The method of claim 14, wherein the biocompatible biodegradable visible light crosslinking photo initiator comprises riboflavin.

16. The method of claim 9, further comprising polycaprolactone.

17. The method of claim 16, wherein the furfuryl amine-conjugated gelatin is blended with the polycaprolactone.

18. The method of claim 17, wherein the furfuryl amine-conjugated gelatin is blended with the polycaprolactone at a ratio of approximately 1:1 by weight.

19. The method of claim 16, wherein the furfuryl amine-conjugated gelatin is connected to and coats the polycaprolactone to define a coaxial scaffold having polycaprolactone core and furfuryl-gelatin sheath.

20. The method of claim 9, wherein the solvent comprises 1,1,1,3,3,3 hexafluoroisopropanol.

* * * * *